US 7,900,625 B2

(12) United States Patent
Kleinstreuer et al.

(10) Patent No.: US 7,900,625 B2
(45) Date of Patent: Mar. 8, 2011

(54) INHALER SYSTEM FOR TARGETED MAXIMUM DRUG-AEROSOL DELIVERY

(75) Inventors: Clement Kleinstreuer, Raleigh, NC (US); Stefan Seelecke, Cary, NC (US)

(73) Assignee: North Carolina State University, Raleigh, NC (US)

( * ) Notice: Subject to any disclaimer, the term of this patent is extended or adjusted under 35 U.S.C. 154(b) by 940 days.

(21) Appl. No.: 11/510,288

(22) Filed: Aug. 25, 2006

(65) Prior Publication Data

US 2007/0044793 A1     Mar. 1, 2007

Related U.S. Application Data

(60) Provisional application No. 60/711,461, filed on Aug. 26, 2005.

(51) Int. Cl.
*A61M 15/08* (2006.01)

(52) U.S. Cl. .......... 128/203.23; 128/200.24; 128/200.14; 128/203.12; 128/203.15

(58) Field of Classification Search ............. 128/203.14, 128/200.11, 200.12, 200.13, 200.14, 200.15, 128/200.16, 200.17, 200.18, 200.19, 200.21, 128/200.22, 200.23, 200.24, 203.12, 203.15; 239/310, 311, 318, 337, 338, 347; 222/52, 222/56, 61, 630, 635

See application file for complete search history.

(56) References Cited

U.S. PATENT DOCUMENTS

| | | | | |
|---|---|---|---|---|
| 2,064,314 | A * | 12/1936 | Morin | 128/200.12 |
| 2,456,451 | A * | 12/1948 | Seaver | 128/203.23 |
| 4,095,596 | A * | 6/1978 | Grayson | 128/203.21 |
| 5,040,527 | A * | 8/1991 | Larson et al. | 128/200.23 |
| 5,355,872 | A | 10/1994 | Riggs et al. | |
| 5,363,842 | A * | 11/1994 | Mishelevich et al. | 128/200.14 |
| 5,404,871 | A * | 4/1995 | Goodman et al. | 128/200.14 |
| 5,437,267 | A | 8/1995 | Weinstein et al. | |
| 5,474,058 | A * | 12/1995 | Lix | 128/200.18 |
| 5,487,378 | A | 1/1996 | Robertson et al. | |
| 5,843,050 | A | 12/1998 | Jones et al. | |
| 5,899,201 | A * | 5/1999 | Schultz et al. | 128/200.23 |
| 5,906,202 | A * | 5/1999 | Schuster et al. | 128/203.23 |
| 6,014,972 | A * | 1/2000 | Sladek | 128/203.12 |
| 6,041,777 | A * | 3/2000 | Faithfull et al. | 128/200.24 |
| 6,190,326 | B1 | 2/2001 | Mckinnon et al. | |
| 6,202,642 | B1 * | 3/2001 | McKinnon et al. | 128/200.23 |

(Continued)

FOREIGN PATENT DOCUMENTS

WO    WO2008/048234     4/2008

OTHER PUBLICATIONS

Zhang et al. *Comparison of micro- and nano-size particle depositions in a human upper airway model* Journal of Aerosol Science, vol. 36, (2005), pp. 211-233.

(Continued)

*Primary Examiner* — Justine R Yu
*Assistant Examiner* — LaToya Louis
(74) *Attorney, Agent, or Firm* — Jenkins, Wilson, Taylor & Hunt, P.A.

(57) ABSTRACT

A smart inhaler system comprising an inhaler device for directed aerosol delivery facilitated by an adaptive nozzle and a mechanism for inhalation waveform modulation is provided. Methods of using the smart inhaler system for delivering an active agent to a target area of a lung of a subject are further provided.

46 Claims, 13 Drawing Sheets

U.S. PATENT DOCUMENTS

| | | | |
|---|---|---|---|
| 6,230,703 B1* | 5/2001 | Bono | 128/200.14 |
| 6,325,475 B1* | 12/2001 | Hayes et al. | 347/2 |
| 6,363,932 B1 | 4/2002 | Forchione et al. | |
| 6,422,236 B1* | 7/2002 | Nilsson et al. | 128/203.15 |
| 6,443,146 B1* | 9/2002 | Voges | 128/200.14 |
| 6,539,937 B1 | 4/2003 | Haveri et al. | |
| 6,682,716 B2 | 1/2004 | Hodges et al. | |
| 6,708,688 B1 | 3/2004 | Rubin et al. | |
| 6,748,945 B2 | 6/2004 | Grychowski et al. | |
| 6,830,046 B2* | 12/2004 | Blakley et al. | 128/200.14 |
| 7,007,689 B2 | 3/2006 | Burns | |
| 7,028,686 B2 | 4/2006 | Gonda et al. | |
| 7,036,500 B2 | 5/2006 | Niles et al. | |
| 7,072,499 B2 | 7/2006 | Deschamps | |
| 7,073,499 B1* | 7/2006 | Reinhold et al. | 128/200.18 |
| 7,077,125 B2 | 7/2006 | Scheuch | |
| 7,080,643 B2 | 7/2006 | Grychowski | |
| 7,090,830 B2 | 8/2006 | Hale et al. | |
| 7,131,441 B1* | 11/2006 | Keller et al. | 128/203.15 |
| 7,316,360 B2* | 1/2008 | Patel et al. | 239/34 |
| 2002/0000225 A1* | 1/2002 | Schuler et al. | 128/200.14 |
| 2002/0062062 A1 | 5/2002 | Belson et al. | |
| 2003/0089368 A1* | 5/2003 | Zhao | 128/200.23 |
| 2003/0168057 A1 | 9/2003 | Snyder et al. | |
| 2004/0050385 A1 | 3/2004 | Bonney et al. | |
| 2004/0097805 A1 | 5/2004 | Verard et al. | |
| 2004/0133231 A1 | 7/2004 | Maitland et al. | |
| 2005/0028814 A1 | 2/2005 | Robertson et al. | |
| 2006/0137681 A1* | 6/2006 | Von Hollen et al. | 128/200.14 |
| 2006/0149350 A1 | 7/2006 | Patel et al. | |
| 2006/0191534 A1* | 8/2006 | Hickey et al. | 128/203.15 |
| 2007/0016069 A1 | 1/2007 | Grunwald | |
| 2007/0151562 A1* | 7/2007 | Jones et al. | 128/203.21 |
| 2007/0156042 A1 | 7/2007 | Unal | |
| 2007/0219480 A1 | 9/2007 | Kamen et al. | |
| 2007/0235029 A1* | 10/2007 | Zhu et al. | 128/203.12 |
| 2008/0245363 A1* | 10/2008 | Korevaar et al. | 128/200.23 |
| 2008/0262467 A1 | 10/2008 | Humphrey et al. | |

OTHER PUBLICATIONS

Zhang et al. *Gas-solid two-phase flow in a triple bifurcation lung airway model International Journal of Multiphase Flow*, vol. 28, (2002), pp. 1021-1046.

Kleinstreuer et al. *Targeted drug aerosol deposition analysis for a four-generation lung airway model with hemispherical tumors Journal of Biochemical Engineering*, vol. 125, (2003), pp. 197-206.

Joseph et al. MEMS in the Medical World. *Sensors Magazine* [online] (Apr. 1997) <http://archives.sensorsmag.com/articles/0497/medical/main.shtml>.

Notification of Transmittal of the International Search Report and the Written Opinion of the International Searching Authority, or the Declaration corresponding to International Application No. PCT/US06/33596 dated Jul. 28, 2008.

Thorne. Inhalation toxicology models of endotoxin- and bioaerosol-induced inflammation, *Toxicology*, vol. 152, pp. 13-23 (2002).

Zhang et al., Computational Analysis of Micron-particle Deposition in a Human Triple Bifurcation Airway Model. *Computer Methods in Biomechanics and Biomedical Engineering*, vol. 5, No. 2, pp. 135-147 (2002).

Kleinstreuer et al., "A new methodology for targeting drug-microspheres in the human respiratory system," International Journal of Heat & Mass Transfer. vol. 51 pp. 5578-5589 (2008).

Notification Concerning Transmittal of International Preliminary Report on Patentability (Chapter I of the Patent Cooperation Treaty) corresponding to International Application No. PCT/US2006/033596 dated Sep. 4, 2008.

Ariel, "Treatment of Inoperable Primary Pancreatic and Liver Cancer by the Intra-Arterial Administration of Radioactive Isotopes ($Y^{99}$ Radiating Microspheres)," Annals of Surgery. vol. 162, No. 2 pp. 267-278 (1965).

Asgharian, B., and Anjilvel, S., "A Monte Carlo Calculation of the Deposition Efficiency of Inhaled Particles in Lower Airways," J. Aerosol. Sci. vol. 25, No. 4 pp. 711-721 (1994).

Asgharian, B., and Anjilvel, S., "The Effect of Fiber Inertia on Its Orientation in a Shear Flow with Application to Lung Dosimetry," Aerosol Science and Technology. vol. 23, No. 3 pp. 282-290 (1995).

Atassi et al., "Multimodality Imaging Following $^{90}$Y Radio-embolization: A Comprehensive Review and Pictorial Essay," Radiographics. vol. 28, No. 1 pp. 81-99 (2008).

Balásházy et al., "Computation of Local Enhancement Factors for the Quantification of Particle Deposition Patterns in Airway Bifurcations," J. Aerosol. Sci. vol. 30, No. 2 pp. 185- 203 (1999).

Balásházy et al., "Local particle deposition patterns may play a key role in the development of lung cancer," J. Appl. Physiol. vol. 94 pp. 1719-1725 (2003).

Benaïssa et al., "Modelling evaporation of multicomponent fuel droplets under ambient temperature conditions," Journal of the Institute of Energy. vol. 75, No. 502 pp. 19-26.

Berlemont et al., "Heat and mass transfer coupling between vaporizing droplets and turbulence using a Lagrangian approach," Int. J. Heat Mass Transfer. vol. 38, No. 16 pp. 3023-3034 (1995).

Bowes, S.M., III, and Swift, D.L., "Deposition of Inhaled Particles in the Oral Airway During Oronasal Breathing," Aerosol Science and Technology. vol. 11, No. 2 pp. 157-167 (1989).

Breedis, C., and Young, G., "The Blood Supply of Neoplasms in the Liver," Am. J. Pathol. pp. 969-985 (1954).

Broday, D.M., and Georgopoulos, P.G., "Growth and Deposition of Hygroscopic Particulate Matter in the Human Lungs," Aerosol Science and Technology. vol. 34 pp. 144-159 (2001).

Buchanan et al., "Rheological effects on pulsatile hemodynamics in a stenosed tube," Computers & Fluids. vol. 29 pp. 695-724 (2000).

Bushi et al., "Hemodynamic Evaluation of Embolic Trajectory in an Arterial Bifurcation: An In-Vitro Experimental Model," Stroke. vol. 36 pp. 2696-2700 (2005).

Campbell et al., "Analysis of the distribution of intra-arterial microspheres in human liver following hepatic yttrium-90 microsphere therapy," Phys. Med. Biol. vol. 45 pp. 1023-1033 (2000).

Cheng et al. , "Dose estimate of inhaled hafnium tritide using the ICRP 66 lung model," Health Physics. vol. 82 pp. 817-824 (2002).

Fan et al., "Gass Collection Efficiency and Entrance Flow Effect of an Annular Diffusion Denuder," Aerosol Science and Technology. vol. 25, No. 2 pp. 113-120 (1996).

Fujioka et al., "Oscillatory Flow and Gas Transport Through a Symmetrical Bifurcation," Journal of Biomechanical Engineering. vol. 123 pp. 145-153 (2001).

Gemci et al., "A Numerical and Experimental Study of Spray Dynamics in a Simple Throat Model," Aerosol Science and Technology. vol. 36 pp. 18-38 (2002).

Gosman, A.D., Ioannides, E., "Aspects of computer simulation of liquid-fueled combustors," Journal of Energy. vol. 7, No. 6 pp. 482-490 (1983) [ABSTRACT].

Grotberg, "Pulmonary Flow and Transport Phenomena," Annu. Rev. Fluid Mech. vol. 26 pp. 529-571 (1994).

Grotberg, "Respiratory Fluid Mechanics and Transport Processes," Annu. Rev. Biomed. Eng. vol. 3 pp. 421-457 (2001).

Hashimoto et al., "Quantitative Tissue Blood Flow Measurement of the Liver Parenchyma: Comparision Between Xenon CT and Perfusion CT," Dig. Dis. Sci. vol. 52 pp. 943-949 (2007).

He, C., and Ahmadi, G., "Particle Deposition in a Nearly Developed Turbulent Duct Flow with Electrophoresis," J. Aerosol Sci. vol. 30, No. 6 pp. 739-758 (1999).

Hübner et al., "Hepatic arterial blood flow velocities: assessment by transcutaneous and intravascular Doppler sonography," Journal of Hepatology. vol. 32 pp. 893-899 (2000).

Ishigami et al., "Does Variant Hepatic Artery Anatomy in a Liver Tranplant Recipient Increase the Risk of Hepatic Artery Complications After Transplantation?" AJR. vol. 183 pp. 1577-1584 (2004).

Kennedy et al., "Pathologic Response and Microdosimetry of $^{90}$Y Microspheres in Man: Review of Four Explanted Whole Livers," Int. J. Radiation Oncology Biol. Phys. vol. 60, No. 5 pp. 1552-1563 (2004).

Kennedy et al., "Recommendations for Radioembolization of Hepatic Malignancies Using Yttrium-90 Microsphere Brachytherapy: A Consensus Panel Report from the Radioembolization Brachytherapy Oncology Consortium," Int. J. Radiation Oncology Biol. Phys. vol. 68, No. 1 pp. 13-23 (2007).

Kim, C.S., and Fisher, D.M., "Deposition Characteristics of Aerosol Particles in Sequentially Bifurcating Airway Models," Aerosol Science and Technology. vol. 31, Nos. 2-3 pp. 198-220 (1999).

Kim et al., "Turbulence statistics in fully developed channel flow at low Reynolds number," J. Fluid Mech. vol. 177 pp. 133-166 (1987).

Kleinstreuer, C., and Zhang, Z., "An Adjustable Triple-Bifurcation Unit Model for Air-Particle Flow Simulations in Human Tracheobronchial Airways," Journal of Biomechanical Engineering. vol. 131 pp. 1-10 (2009).

Kulik et al., "Yttrium-90 Microspheres (TheraSphere®) Treatment of Unresectable Hepatocellular Carcinoma: Downstaging to Resection, RFA and Bridge to Transplantation," Journal of Surgical Oncology. vol. 94 pp. 572-586 (2006).

Li, A., and Ahmadi, G., "Dispersion and Deposition of Spherical Particles from Point Sources in a Turbulent Channel Flow," Aerosol Science and Technology. vol. 16, No. 4 pp. 209-226 (1992).

Liu et al., "Modeling the bifurcating flow in an asymmetric human lung airway," Journal of Biomechanics. vol. 36 pp. 951-959 (2003).

Mabotuwana et al., "A model of blood flow in the mesenteric arterial system," BioMedical Engineering Online. vol. 6, No. 17 pp. 1-12 (2007).

MacInnes, J.M., and Bracco, F.V., "Stochastic particle dispersion modeling and the tracer-particle limit," Phys. Fluids A. vol. 4, No. 12 pp. 2809-2824 (1992).

Matida et al., "Statistical simulation of particle deposition on the wall from turbulent dispersed pipe flow," International Journal of Heat and Fluid Flow. vol. 21 pp. 389-402 (2000).

Muller, J.H., and Rossier, P.H., "A New Method for the Treatment of Cancer of the Lungs by Means of Artificial Radioactivity," Acta radiologica. vol. 35, Nos. 5-6 pp. 449-468 (1951).

Murthy et al., "Yttrium-90 Microsphere Therapy for Hepatic Malignancy: Devices, Indications, Technical Considerations, and Potential Complications," Radiographics. vol. 25, No. 1 pp. S41-S55 (2005).

Nowak et al., "Computational Fluid Dynamics Simulation of Airflow and Aerosol Deposition in Human Lungs," Annals of Biomedical Engineering. vol. 31 pp. 374-390 (2003).

Ounis et al., "Dispersion and Deposition of Brownian Particles from Point Sources in a Simulated Turbulent Channel Flow," Journal of Colloid and Interface Science. vol. 147, No. 1 pp. 233-250 (1991).

Pedley, "Pulmonary Fluid Dynamics," Ann. Rev. Fluid Mech. vol. 9, pp. 229-274 (1977).

Pedley et al., "Flow and pressure drop in systems of repeatedly branching tubes," J. Fluid Mech. vol. 46, No. 2 pp. 365-383 (1971).

Phalen, R.F., and Oldham, M.J., "Methods for modeling particle deposition as a function of age," Respiration Physiology. vol. 128 pp. 119-130 (2001).

Radeleff et al., "Acute Increase in Hepatic Arterial Flow During TIPS Identified by Intravascular Flow Measurements," Cardiovasc. Intervent. Radiol. vol. 32 pp. 32-37 (2009).

Renotte et al., "Numerical 3D analysis of oscillatory flow in the time-varying laryngeal channel," Journal of Biomechanics. vol. 33 pp. 1637-1644 (2000).

Salem et al., "Radioembolization with 90Yttrium Microspheres: A State-of-the-Art Brachytherapy Treatment for Primary and Secondary Liver Malignancies," Journal of Vascular and Interventional Radiology. vol. 17, No. 8 pp. 1251-1278 (2006).

Sato et al., "Unresectable Chemorefractory Liver Metastases: Radioembolization with $^{90}Y$ Microspheres—Safety, Efficacy, and Survival," Radiology. vol. 247, No. 2 pp. 507-515 (2008).

Shuen et al., "Evaluation of a Stochastic Model of Particle Dispersion in a Turbulent Round Jet," AIChE Journal. vol. 29, No. 1 pp. 167-170 (1983).

SM5108. Silicon Microstructures Incorporated. 2003-2004; pp. 1-2.

Tanaka et al., "Spatial and Temporal Variation of Secondary Flow During Oscillatory Flow in Model Human Central Airways," Journal of Biomechanical Engineering. vol. 121 pp. 565-573 (1999).

Wang, Y., and James, P.W., "On the effect of anisotropy on the turbulent dispersion and deposition of small particles," International Journal of Multiphase Flow. vol. 25 pp. 551-558 (1999).

Webb et al., "Control of SMA actuators in dynamic environments," Part of the SPIE Conference on Mathematics and Control in Smart Structures, Newport Beach, California. Mar. 1999. vol. 3667 pp. 278-289.

Yu et al., "Fluid Flow and Particle Diffusion in the Human Upper Respiratory System," Aerosol Science and Engineering. vol. 28, No. 2 pp. 146-158 (1998).

Notification of Transmittal of the International Search Report and the Written Opinion of the International Searching Authority, or the Declaration corresponding to International Application No. PCT/US2010/043552 dated Sep. 24, 2010.

* cited by examiner (a) PARTICLE RELEASE POSITION AT THE MOUTH INLET (b) RESULTING PARTICLE DEPOSITION PATTERNS IN THE ORAL AIRWAY ($Q_{in}$=15 l/min)

(c) RESULTING PARTICLE DEPOSITION PATTERNS IN THE BRONCHIAL AIRWAY G0 TO G3 WITH LOCAL TUMORS (r/R=1.25, $Q_{in}$=15 l/min)

NORMAL CASE ($d_p$=7μm)

NORMAL CASE

NORMAL CASE
DF (TARGETED TUMOR) =0.7%
DF (NON-TARGETED SITES) =4.0%
TARGETED TUMOR SITE

DF = 1.9%

CONTROLLED CASE ($d_p$=7μm)
d=100μm

CONTROLLED CASE

CONTROLLED CASE
DF (TARGETED TUMOR) =73.8%
DF (NON-TARGETED SITES) =2.5%
TARGETED TUMOR SITE

A. INLET
RELEASE POSITION 60° RELEASE POSITION 165° RELEASE POSITION 240°
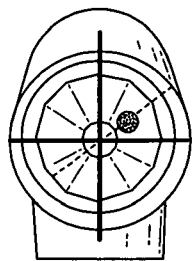 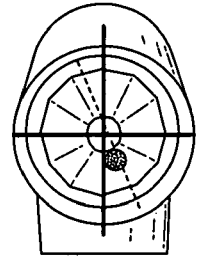 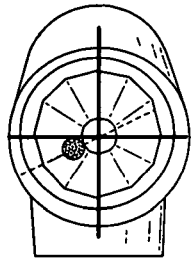
B. LEFT BRANCH
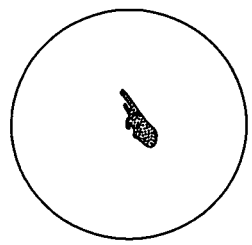 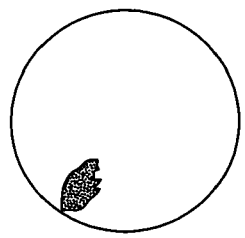 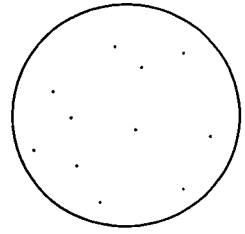
C. RIGHT BRANCH
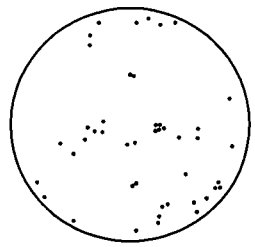 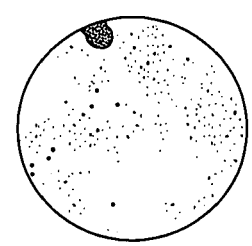 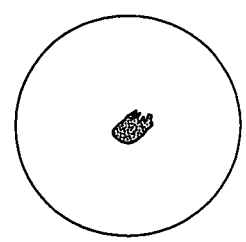
FIG. 10

INHALER SYSTEM FOR TARGETED MAXIMUM DRUG-AEROSOL DELIVERY

CROSS-REFERENCE TO RELATED APPLICATIONS

This application claims the benefit of U.S. Provisional Patent Application Ser. No. 60/711,461, filed Aug. 26, 2005; the disclosure of which is incorporated herein by reference in its entirety.

GOVERNMENT INTEREST

The presently disclosed subject matter was made with U.S. Government support under Grant Nos. BES-0201271 awarded by the National Science Foundation, FA 9550-04-1-0422 awarded by the U.S. Air Force Office of Scientific Research, and 1R21GM074651-01 and 8R21EB006717-02 awarded by the National Institutes of Health. As such, the U.S. Government has certain rights in the present subject matter.

TECHNICAL FIELD

The presently disclosed subject matter relates to inhaler systems. In particular, the presently disclosed subject matter relates to inhaler systems capable of producing a controlled inhaled aerosol stream which can be directed to a desired lung target area with minimization of parasitic deposition.

BACKGROUND

Chronic obstructive pulmonary disease was in 1998 the fourth leading cause of death in the United States (see National Center for Health Statistics Report; 48 (11), (1998)). There has also been an astonishing increase over the last 20 years in asthma and cancer cases among children (see EPA Report 240-R-00-006; December 2000).

Inhalation of therapeutic particles, such as, but not limited to, drug aerosols, is a standard procedure for the treatment of lung airway inflammations and obstructions. This procedure is also now becoming a novel way to combat cancer, diabetes, AIDS, and other diseases, as well as for rapid pain management as inhalation of therapeutics can provide a very effective mechanism of systemic delivery. Existing drug aerosol delivery devices, however, including those that attempt to target specific areas in the lung, exhibit poor efficiencies (e.g., efficiencies ranging from about 5% to about 20%). Consequently, significant portions of the often-aggressive and expensive therapeutic agent used to combat diseases such as cancer, diabetes, and AIDS can deposit on healthy tissue.

For more than 40 years, the most commonly used device for administering therapeutic agents to combat such lung diseases has been the pressurized metered dose inhaler (pMDI). In a pMDI, a propellant (e.g., a non-CFC, such as HFA 134a) ejects, from a pressurized container via a valve, a metered dose of drug in solution (or colloidally suspended) into a spacer where an aerosolized plume is formed and then inhaled. Despite several improvements over the past decades concerning pMDI propellants, actuation mechanisms, and plume modifiers (see Crowder et al., 2001; and Edwards and Dunbar, 2002), pMDI devices suffer from systemic disadvantages (Keller, 1999); for example, the very low target deposition efficiencies, the relatively high aerosol speed, and the requirement for patients to synchronize their breathing inspiration with the actuation of the aerosol device.

Jet and ultrasonic nebulizers have also been used for administering therapeutic agents. These devices deliver therapeutic agents in the form of small droplets or a mist, suitable for single or multiple-dose, deep lung penetration of drugs by breath-actuation. Research efforts thus far have focused on the development of portable, battery-powered jet and ultrasonic aerosol generators. Unfortunately, these devices typically provide unsatisfactory deposition efficiencies.

Use of powder aerosols, either loaded by the user into a dry powder inhaler (DPI) or stored in the device, is another approach for administering therapeutic agents. In passive DPIs, the motion of the inhaled air generates powder particle entrainment and breakup, whereas in active DPIs, stored energy (e.g., blister packs) assists during inhalation in drug powder dispersion (Dunbar et al., 1998). Again, like pMDIs and jet and ultrasonic nebulizers, DPIs typically do not provide adequate targeted deposition efficiencies.

Thus, there is a need in the art for improved aerosol delivery devices, especially aerosol delivery devices that can target specific areas in the lung.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In one embodiment of the presently disclosed subject matter, a method of delivering an active agent to a target area of a lung of a subject in need thereof is provided. In some embodiments, the method comprises providing an inhaler system for directing to a subject a controlled aerosol stream comprising an active agent and regulating a release position of the controlled aerosol stream from the inhaler system to deliver the active agent to a target area of a lung of the subject. In some embodiments, the active agent comprises one or more physical characteristics selected from the group consisting of: a particle size of from about 1 μm to about 20 μm; a substantially spherical shape; and a low density.

In another embodiment of the presently disclosed subject matter, an inhaler device for targeted aerosol stream release is provided. In some embodiments, the inhaler device comprises: an outer tube having an inlet at one end, an outlet at an opposing end, and a wall joining the inlet and the outlet comprising one or more air inlet perforations which provide for passage of inhalation airflow into an interior of the outer tube; an adaptive nozzle positioned within the interior of the outer tube and having a nozzle base inlet engaged with the outer tube inlet and a nozzle tip outlet proximal to the outer tube outlet, wherein the nozzle tip outlet and the nozzle base inlet are in flow communication and adapted for passage of an aerosol stream therebetween; and one or more actuators operationally linked to the adaptive nozzle, wherein the one or more actuators can position the nozzle tip outlet and thereby target the aerosol stream release from the inhaler device.

In some embodiments, the inhaler device comprises an inhalation airflow control mechanism for varying a cross-section of one or more of the outer tube air inlet perforations, thereby permitting control of the inhalation airflow to generate a desired inhalation waveform. Further, in some embodiments, the inhalation airflow control mechanism is provided in an inhaler device for generating a desired inhalation waveform, in the absence of an adaptive nozzle. In some embodiments, the inhalation airflow control mechanism comprises: an inner tube comprising one or more air inlet perforations, wherein the inner tube is positioned within the interior of the outer tube and slidingly engages an inner surface of the outer tube wall; and one or more actuators operationally linked to the inner tube, wherein the one or more actuators can slidingly position the inner tube to vary the alignment of the one or more inner tube air inlet perforations with the outer tube air inlet perforations, thereby varying the cross-section of one or more of the outer tube air inlet perforations. In some embodiments, the one or more inner tube actuators comprise an active material, such as for example an active material selected from the group consisting of a shape memory alloy (e.g., an alloy of nickel and titanium), a shape memory polymer, a magnetostrictive material, and a piezoceramic material.

In some embodiments, the inhaler device comprises one or more micropressure sensors positioned proximal to the outer tube outlet, which can detect an inhalation waveform from inhalation airflow flowing through the outer tube and transmit a signal to the inner tube actuators. The inner tube actuators can vary the position of the inner tube to change the alignment of the inner tube air inlet perforations with the outer tube air inlet perforations, thereby altering the inhalation waveform in response to the signal. The signal from the micropressure sensors can be transmitted to a control logic (e.g. a proportional-integral-derivative (PID) algorithm), which interprets the signal and transmits an actuator control signal to the inner tube actuators. In some embodiments, the control logic is in operational communication with computational fluid-particle dynamics results that determine one or more of the desired inhalation waveform and the desired position of the adaptive nozzle to direct the aerosol stream to a desired target area in a lung of a subject.

In some embodiments, the adaptive nozzle comprises a flexible polymer that permits flexing of the adaptive nozzle. In some embodiments, the one or more adaptive nozzle actuators comprise a first set of adaptive nozzle actuators that position the nozzle tip outlet within the outer tube and a second set of adaptive nozzle actuators that flex the adaptive nozzle such that the nozzle tip outlet is axially aligned with the outer tube outlet after positioning. The one or more adaptive nozzle actuators can comprise an active material, such as for example a shape memory alloy (e.g., an alloy of nickel and titanium), a shape memory polymer, a magnetostrictive material, or a piezoceramic material. In other embodiments, the adaptive nozzle can be rotated in an orbit around a central long axis of the outer tube and positioned at one or more desired orbital locations on the orbit.

In another embodiment of the presently disclosed subject matter, an inhaler system for targeted aerosol stream release is provided. In some embodiments, the inhaler system comprises: an aerosol source; an aerosol injection system in flow communication with the aerosol source; and an inhaler device in flow communication with the aerosol injection system. The inhaler device can in some embodiments comprise: an outer tube having an inlet at one end, an outlet at an opposing end, and a wall joining the inlet and the outlet comprising one or more air inlet perforations which provide for passage of inhalation airflow into an interior of the outer tube; an adaptive nozzle positioned within the interior of the outer tube and having a nozzle base inlet engaged with the outer tube inlet and a nozzle tip outlet proximal to the outer tube outlet, wherein the nozzle tip outlet and the nozzle base inlet are in flow communication and adapted for passage of an aerosol stream therebetween; and one or more actuators operationally linked to the adaptive nozzle, wherein the one or more actuators can position the nozzle tip outlet and thereby target aerosol stream release from the inhaler device.

In some embodiments, the aerosol source comprises a source selected from the group consisting of a pressurized metered dose inhaler (pMDI), a jet nebulizer (JN) and a dry powder inhaler (DPI).

In some embodiments, the aerosol injection system comprises a controllable reservoir chamber having an inlet in flow communication with the aerosol source and an outlet in flow communication with the inhaler device. In some embodiments, the aerosol injection system comprises: a pressure sensor that measures pressure within the controllable reservoir chamber; an inlet valve for controlling entry of an aerosol into the controllable reservoir chamber through the reservoir chamber inlet; and an outlet valve for controlling release of the aerosol from the controllable reservoir chamber through the reservoir chamber outlet, wherein the pressure sensor measures pressure within the reservoir chamber and regulates opening and closing of the inlet valve and the outlet valve in order to maintain a desired pressure within the reservoir chamber. In some embodiments, the inlet and outlet valves each comprise an active material actuator, such as for example a thin film actuator. In some embodiments, the active material actuator comprises an active material selected from the group consisting of a shape memory alloy, a shape memory polymer, a magnetostrictive material, and a piezoceramic material.

Accordingly, it is an object of the presently disclosed subject matter to provide an inhaler system for targeted drug-aerosol delivery. This object is achieved in whole or in part by the presently disclosed subject matter.

An object of the presently disclosed subject matter having been stated above, other objects and advantages will become apparent to those of ordinary skill in the art after a study of the following description of the presently disclosed subject matter and non-limiting examples.

BRIEF DESCRIPTION OF THE DRAWINGS

FIGS. 6A-6C are diagrams of a simulation-based drug delivery design for the upper airway, starting from the mouth. A hemispherical tumor was placed in generation G2, comparing drug aerosol deposition fractions on the tumor surface for a case utilizing a simulated standard pMDI (normal case) and a simulated smart inhaler system as disclosed herein (controlled case). FIG. 6A shows particle release position at the mouth inlet. FIG. 6B shows resulting particle deposition patterns in the oral airway. FIG. 6C shows resulting particle deposition patterns in the bronchial airway G0 to G3 with local tumors.

FIGS. 10A-10C show results of targeted aerosol stream release. FIG. 10A is a series of schematic drawings showing nozzle position for targeted release of the aerosol stream. FIGS. 10B and 10C are photographs showing particle locations at the outlet of left (FIG. 10B) and right branches (FIG. 10C) after first bifurcation (B1, as labeled in FIG. 11B). Flow rate was 8 slpm.

DETAILED DESCRIPTION

Figure 1:
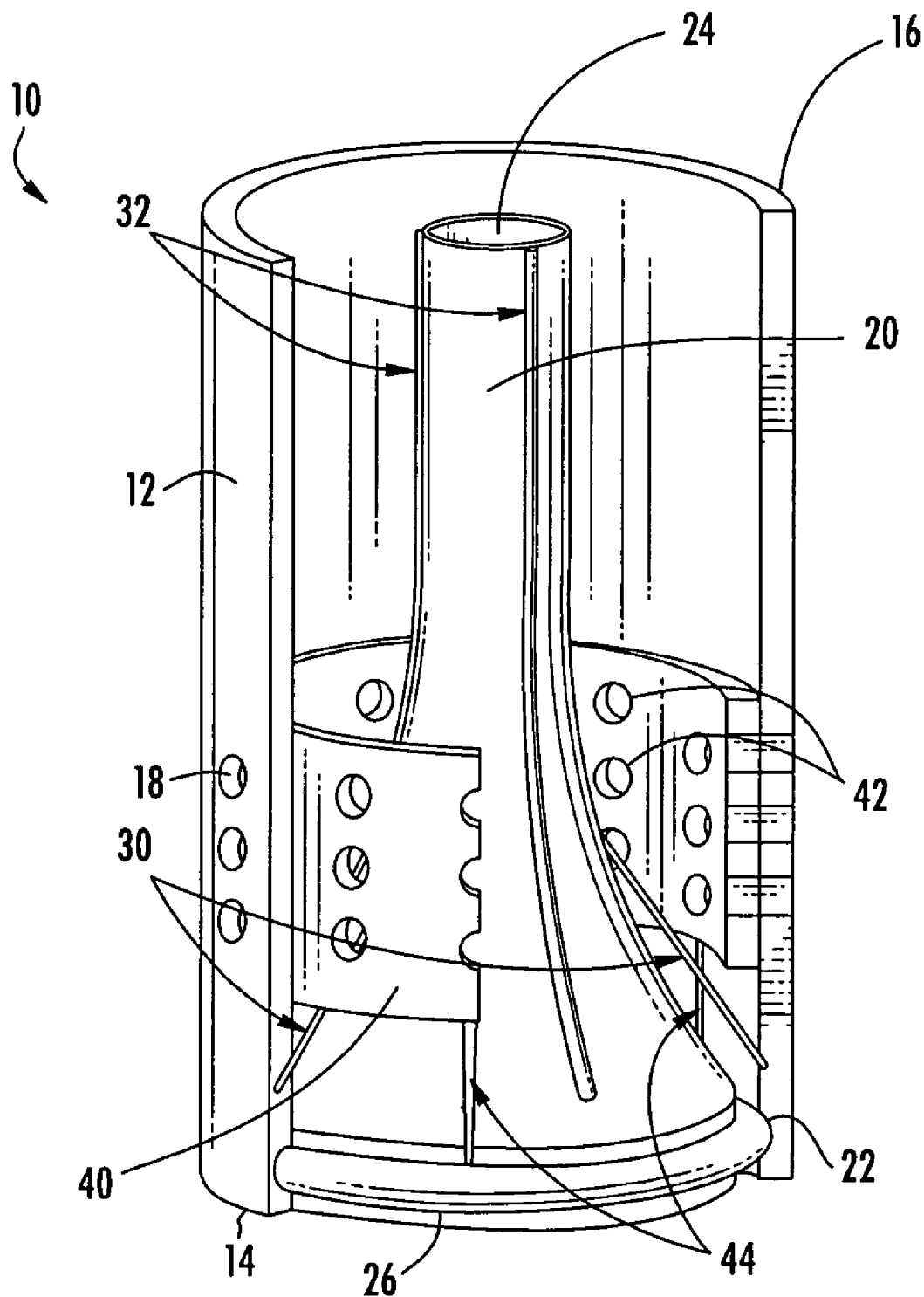
FIG. 1 is a cut-away perspective view of one embodiment of an inhaler device as disclosed herein.

The presently disclosed subject matter provides a smart inhaler system, which can in representative embodiments fulfill two tasks simultaneously: the provision of substantially maximum drug particle deposition on desired lung target sites and the minimization of deposition of potentially very aggressive drugs on healthy lung tissue by targeted release of an aerosol stream from the inhaler system. Further, by automatically modifying within the inhaler system inhalation airflow produced by a subject's inhalation, the presently disclosed smart inhaler system generates a controlled inhalation waveform, thereby reducing or even avoiding extra training phases. The avoidance of such extra training phases can be especially beneficial in the treatment of young children and/or the elderly.

In contrast to conventional approaches, which use turbulent flow already in the mouth inlet cross section (i.e., the inhaler outlet opening) to increase mixing of inhalation airflow and aerosols (Finley, 2001; Crowder, 2001; and Clark, 2004), computational fluid-particle dynamics (CFPD) analysis utilized by the presently disclosed subject matter predicts a correlation between aerosol characteristics and aerosol stream release position into an inhalation airflow and the deposition location, when powered by a predetermined laminar inhalation waveform. The analysis suggests that three factors should be considered for targeted delivery, i.e., optimal aerosol characteristics (e.g., size, shape, and density of active agent particles), control of the particle release positions, and flow control of inhalation waveform. In some embodiments, the presently disclosed subject matter can address each of these factors, including in particular the second factor and/or the third factor, i.e., control of the particle release positions and/or flow control of the inhalation waveform utilizing a smart inhaler system of the presently disclosed subject matter for targeted delivery of an active agent in an aerosol stream.

The first factor, i.e., aerosol characteristics, can in some embodiments, be addressed through the selection or production of an active agent (alone or in combination with a carrier) comprising desired physical characteristics. In some embodiments, desired physical characteristics of the active agent include, but are not limited to a particle size of from about 1 μm to about 10 μm or from about 5 μm to about 20 μm (e.g., 7 μm or 8 μm), a substantially spherical shape, and a low density (e.g., a density comparable to the surrounding carrier medium which can minimize sedimentation and impaction).

Accordingly, the presently disclosed subject matter provides in some embodiments a method of delivering an active agent to a target area of a lung of a subject in need thereof. In some embodiments, the method comprises providing an inhaler system (e.g., a smart inhaler system) for directing to a subject a controlled aerosol stream comprising an active agent; and regulating a release position of the controlled aerosol stream from the inhaler system into an inhalation airflow to deliver the active agent to a target area of a lung of the subject.

The presently disclosed subject matter provides a "smart inhaler system", which can increase targeted deposition efficiencies over current inhalers known in the art. Current inhaler systems can at best broadly target lung regions, such as the upper (bronchial) or lower (alveolar) lung. In contrast, the presently disclosed inhalers provide for targeting regions in specific generations (i.e., lung branches) in either the left or the right lobe of the lung, if desired. Together with drastically minimized parasitic wall deposition in the oral airways and on other healthy tissue, the presently disclosed smart inhaler system enables safer and more efficient treatment of lung cancer and other respiratory diseases through targeted drug delivery. In addition, the system also creates a platform for the oral intake of various other kinds of active agents, such as insulin, with desirable efficiency.

Further, in some embodiments the presently disclosed smart inhaler system can automatically detect and adapt to a subject's breathing pattern thereby providing a desired inhalation waveform, and reducing and/or even removing the need for individual training and the associated intake uncertainties. An "inhalation waveform" as the term is used herein refers to a measure of air flow over time (e.g., liters per minute). Normally, inhalation waveforms can vary over the length of a breath, having a peak somewhere toward the middle of a breath and decreasing on either end, which in turn is mirrored in an inhaler outlet where an aerosol stream is injected during an actuation of an inhaler device. In addition, different users, e.g. healthy vs. infirm and children vs. adults, produce different waveforms that can affect targeted delivery of the active agent. As such, a desired, ideal, or optimal waveform can be calculated and the presently disclosed smart inhaler system can measure and adapt an inhalation waveform to a desired inhalation waveform. In some embodiments, a "desired inhalation waveform" is a waveform that can facilitate uniform (e.g., rectangular graphed waveform) laminar flow (e.g., an inhalation flow rate ($Q_{in}$)≦12 Liters (L)/minute (min)) of the air stream produced by inhalation through the inhaler (i.e., the inhalation airflow) during substantially all of the time period during which the aerosol stream is being directed into the inhalation airflow. For example, in some embodiments, a desired inhalation waveform is one in which the flow rate is substantially constant and from about 6 L/min to about 10 L/min, and in some embodiments about 8 L/min.

The performance characteristics of the presently disclosed smart inhaler system can be realized in some embodiments through: (1) a combination of sensors; (2) an adaptive smart inhaler device and a reservoir chamber, both of which can be actuated in some embodiments by shape memory alloy (SMA) actuators; and (3) a control logic, which can be based on experimentally validated predictions of a computer simulation model of targeted lung deposition.

In some embodiments, the presently disclosed smart inhaler system implements a controlled air-particle stream, which directs inhaled therapeutic agents, such as drug aerosols, to a desired lung target area with maximum deposition efficiency independent of an individual subject's inhalation pattern. The inhaler system can work in conjunction with an aerosol source and can comprise in some embodiments two components: (i) an aerosol injection system, which regulates the pressure/velocity and particle distribution of the aerosol source employed; and (ii) an inhaler device, having in some embodiments control mechanisms for (a) producing the desired inhalation waveform independent of a subject's breathing mode and (b) delivering into the inhalation waveform the embedded particle aerosol stream from an optimal release position.

To achieve a desired aerosol efficiency at targeted lung areas, such as for example more than about 45%, the inhaler device, which also can function as a mouth-piece, can be attached, e.g., by a clamp, either directly to an existing aerosol source, for example, a jet nebulizer (JN), a pressurized metered dose inhaler (pMDI) or a dry powder inhaler (DPI), and the like, or to an aerosol injection system, which in turn is attached to an aerosol source. The inhaler device can be regulated for a specific aerosol type and disease and helps to guide the therapeutic agent to the desired lung target area independent of the subject's breathing pattern.

In addition to respiratory therapies, an increasing number of therapeutic agents could benefit from lung delivery via the presently disclosed smart inhaler system, including anti-tubercular agents, vaccines, morphine and other therapeutic agents for pain management, growth hormones, insulin for diabetes therapy, beta-interferon, and oligonucleotides for cystic fibrosis gene therapy, and the like.

Accordingly, in some embodiments, a combination of a smart inhaler device and an aerosol injection system can be used to implement the mechanisms for the control of inhalation waveform and particle release position. This modular concept allows for the accommodation of different aerosol sources, e.g., JN, DPI, and pMDI, as well as adaptation of different subject's breathing patterns. Suitable aerosol sources known in the art, include, but are not limited to, jet and ultrasonic nebulizers, which deliver drugs in form of small droplets or a mist, suitable for single or multiple-dose, deep lung penetration of drugs by breath-actuation. Further, use of powder aerosols, either loaded by the user into a dry powder inhaler (DPI) or stored in the device, is another approach. In passive DPIs, the motion of the inhaled air generates powder particle entrainment and breakup, whereas in active DPIs, stored energy (e.g., blister packs) assists during inhalation in drug powder dispersion (Dunbar et al., 1998).

The presently disclosed subject matter provides in some particular embodiments a smart inhaler system comprising an aerosol source, an aerosol injection system and a smart inhaler device, all in flow communication. In some embodiments, the aerosol injection system and inhaler device are attached to a conventional drug-aerosol source, such as a JN, a pMDI or a DPI.

The smart inhaler device can comprise an outer tube having an inlet at one end and an open outlet that can act as a mouth piece at an opposing end. The outer tube can further comprise one or more air inlet perforations which provide for passage of inhalation airflow into an interior of the outer tube.

In some embodiments, based on in situ pressure measurements, the optimal, computationally predetermined inhalation waveform can be generated in real-time utilizing an inhalation airflow control mechanism for varying a cross-section of one or more of the outer tube air inlet perforations, thereby permitting control of the inhalation airflow to generate the predetermined inhalation waveform within the inhaler device, and in particular, at the location of aerosol stream release. In some embodiments, the inhalation airflow control mechanism comprises an actuated inner tube comprising air inlet perforations, which slides relative to the perforations in the outer tube to vary the cross-sections of the outer tube perforations.

The targeted drug-aerosol stream release from a computationally predetermined position/segment of the outlet cross-section of the outer tube/mouthpiece, which can be selected based on a desired target area of the lung of a subject, can be achieved in some embodiments with an adaptive nozzle positioned within the outer tube.

In some embodiments, the adaptive nozzle comprises a nozzle tip outlet, which can be deflected by one or more actuators and hence optimally positioned within the outer tube. In another embodiment, targeted drug-aerosol stream release can be achieved utilizing an adaptive nozzle with variable exit diameters and which is positioned substantially and in some embodiments perfectly parallel to the inhaler tube wall. Determination of targeted release positions from correlated positions on orbits with critical radii allows for constructing the nozzle so as to rotate around a central long axis and arrest on the selected orbits and at orbital locations (see FIG. 12 and Example 5, for example). Changes in nozzle exit diameter and orbital positioning can be implemented via various mechanisms. Non-limiting examples for orbital positioning include ball-and-spring-loaded disk/ratchet or a precision-gear mechanism. Different radial settings can achieve target-specific orbits.

The computationally predetermined drug-aerosol stream characteristics and release positions are a function of a subject's lung morphology, type of drug, and deposition site. As used herein, the term "subject" refers to both human beings and animals (e.g., mammalian subjects) for medical, veterinary, testing and/or screening purposes.

The inhaler device can also be equipped with one or more micropressure sensors to detect the inhalation waveform from inhalation airflow flowing through the outer tube, which can be positioned in some embodiments proximal to the outer tube outlet, such as for example in the outlet cross-section. Exemplary micropressure sensors suitable for use with the presently disclosed inhaler device include, but are not limited to, silicon micromachined piezoresistive pressure sensing chips, such as those available from Silicon Microstructures, Inc. (Milpitas, Calif., U.S.A.). Based on this information, the cross-section of the air inlets can be varied, such as by varying the position of the perforated inner sliding tube by actuators receiving a signal from the micropressure sensors to transform the initial inhalation airflow waveform into an inhalation waveform that corresponds to uniform laminar flow necessary for optimal air-particle transport. In some embodiments, the actuators vary the position of the inner tube to change the alignment of the inner tube air inlet perforations with the outer tube air inlet perforations to produce the desired inhalation waveform.

In some embodiments, active materials can be utilized. Active materials include for example shape memory alloys (SMA), shape memory polymers, piezoceramic materials or magnetostrictive materials for actuation, and in some embodiments for sensing as well, which allows for the development of highly integrated intelligent systems.

An illustrative example of actuation by active materials is the linear actuation capability of an SMA wire actuator. This material is known to exhibit the highest work output per volume of all known actuation mechanisms, see, e.g. Hollerbach et al. (1992). It can easily be stretched at low temperatures, but upon thermal activation, which can be effected by low-voltage electric power, it contracts, very much like a "metal muscle". Thus, it not only replaces an entire apparatus of gears and other transmission components, but at the same time also provides high actuation force and stroke, is lightweight, and can easily be embedded into structures in a highly flexible way.

Moreover, a prominent SMA, nickel titanium alloy (NiTi), is known for its high biocompatibility, and these attractive features have led to a number of applications in the biomedical field, which range from already well-established applications, like stents and orthodontal braces (Duerig et al., 1999), to more advanced systems like smart endoscopes actuated by SMA wires (Reynaerts et al., 1999), and micro drug-dosage systems based on SMA thin film pumps (Benard et al., 1998; Makino et al., 2001; Xu et al., 2001).

Now with reference to FIG. 1, a particular embodiment of a smart inhaler device 10 is shown. Inhaler device 10 comprises an outer tube 12 having an inlet 14 at one end and an outlet 16 at an opposing end of inhaler device 10. Outer tube 12 can comprise a plurality of air inlet perforations 18 through the wall of outer tube 12. Outer tube 12 serves as a mouth piece, in that a subject places their mouth against or over outlet 16 and inhales, drawing air through air inlet perforations 18 to create an inhalation airflow through the interior of outer tube 12 and into the subject's lungs.

An aerosol stream comprising an active agent is delivered from an aerosol source through an adaptive nozzle 20 and into the inhalation airflow for targeted delivery to a target area of lung of the subject. As shown in FIG. 1, adaptive nozzle 20 is positioned within the interior of outer tube 12. Adaptive nozzle 20 has a nozzle base inlet 22 that sealingly engages outer tube inlet 14 and a nozzle tip outlet 24 that is in axial alignment with outer tube outlet 16. That is, nozzle tip outlet 24 has a long-axis that is parallel to a long-axis of outer tube 12, which is perpendicularly bisected by outer tube outlet 16.

Nozzle base inlet 22 can be positioned in flow communication, directly or indirectly, with an aerosol source. Nozzle tip outlet 24 is positioned in proximity to outer tube outlet 16 so that the aerosol stream is optimally merged with the inhalation airflow.

A sealing member 26 connects nozzle base inlet 22 with outer tube outlet 16 to provide an airtight seal between outlet 16 and nozzle base inlet 22. Sealing member 26 can be a flexible polymeric O-ring, which can provide both sealing functionality and flexibility to provide mobility to adaptive nozzle 20 within outer tube 12.

As previously disclosed, the smart inhaler system can increase targeted deposition efficiencies over other inhalers known in the art in part through the controlled delivery of the aerosol stream into the inhalation airflow through calculated positioning of nozzle tip outlet 24 within outer tube 12. Actuators can be utilized to position adaptive nozzle 20, and in particular nozzle tip outlet 24, to the desired optimum release position for delivery of the aerosol into the inhalation airflow. Due to space limitations present in some embodiments of inhaler device 10, it can be desirable in some embodiments to utilize actuators comprising active materials. Exemplary active materials that can be utilized with the presently disclosed subject matter include, but are not limited to, shape memory alloys, shape memory polymers, magnetostrictive materials, and piezoceramic materials. In some embodiments, when shape memory alloys are employed, an alloy of nickel and titanium (NiTi) can be utilized. As shown in FIG. 1, shape memory alloys (SMAs) can be fabricated as wires, such as for example FLEXINOL® wires produced by Dynalloy, Inc. (Costa Mesa, Calif., U.S.A.), and thereby act as SMA actuators. For example, as shown in the particular embodiment illustrated in FIG. 1, a plurality of SMA actuators are operationally linked to adaptive nozzle 20 near nozzle base inlet 22 and to the inner wall of outer tube 12.

In the embodiment illustrated in FIG. 1, a set of three SMA actuators 30 are utilized (only two of which are visible in FIG. 1) to deflect the entire adapter nozzle 20 to a desired position within outer tube 12. A second set of SMA actuator wires 32 can further be utilized, as shown in FIG. 1, to further flex adaptive nozzle 20, in combination with repositioning the entire structure of adaptive nozzle 20, as accomplished by SMA actuators 30. Actuators 32 can be axially bonded to adaptive nozzle 20 along at least a portion of a long-axis of adaptive nozzle 20 and can therefore bend adaptive nozzle 20 such that nozzle tip outlet 24 remains axially aligned with outer tube outlet 16 to ensure aerosol stream release is parallel to (laminar flow) the inhalation airflow.

To prevent premature mixing, wall deposition, or particle coagulation, in some embodiments, adaptive nozzle 20 comprises a flexible material, such as a flexible polymeric material, to permit flexing of adaptive nozzle 20 by actuators 32. Nozzle 20 should present a reasonable compromise between a certain flexibility to enable the necessary deformation and sufficient stiffness to maintain the required shape in the airflow. One non-limiting example of a suitable elastomeric material for use in the construction of flexible nozzle 20 includes silicon rubber. It can be desirable to provide in some embodiments inner surfaces of adaptive nozzle 20, and in some instances outer tube 12 as well, with higher finish tolerances in order to avoid problems with wall deposition of aerosol particles and turbulence effects. Alternatively, or in combination, the inner surfaces can be coated with compositions that facilitate reduction of turbulence and/or aerosol deposition, as generally known by those of skill in the art.

Figure 2A:
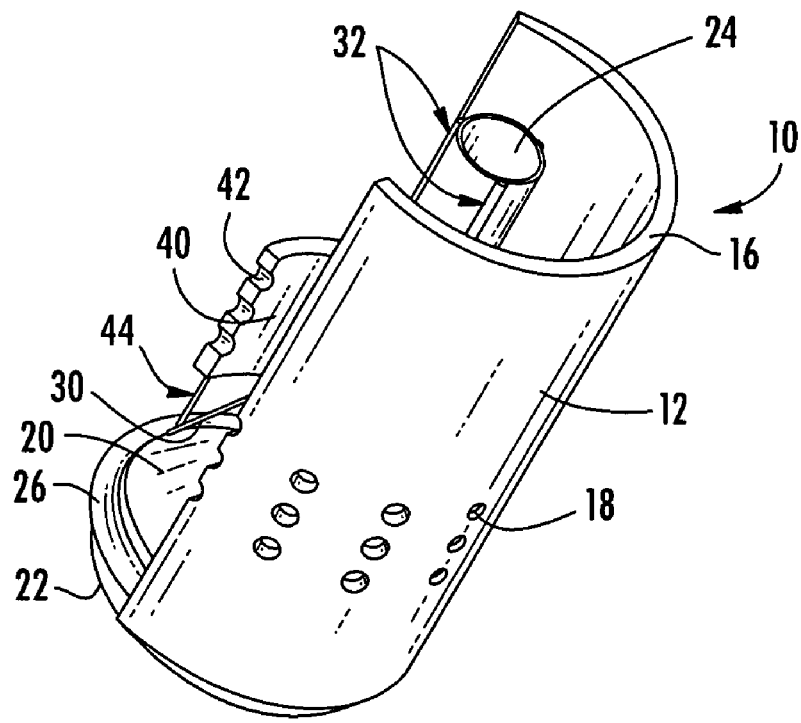
FIGS. 2A and 2B are cut-away perspective views of one embodiment of an inhaler device as disclosed herein showing the adaptive nozzle in a neutral position (FIG. 2A) and in an altered position as a result of repositioning by SMA actuators (FIG. 2B).
Figure 2B:
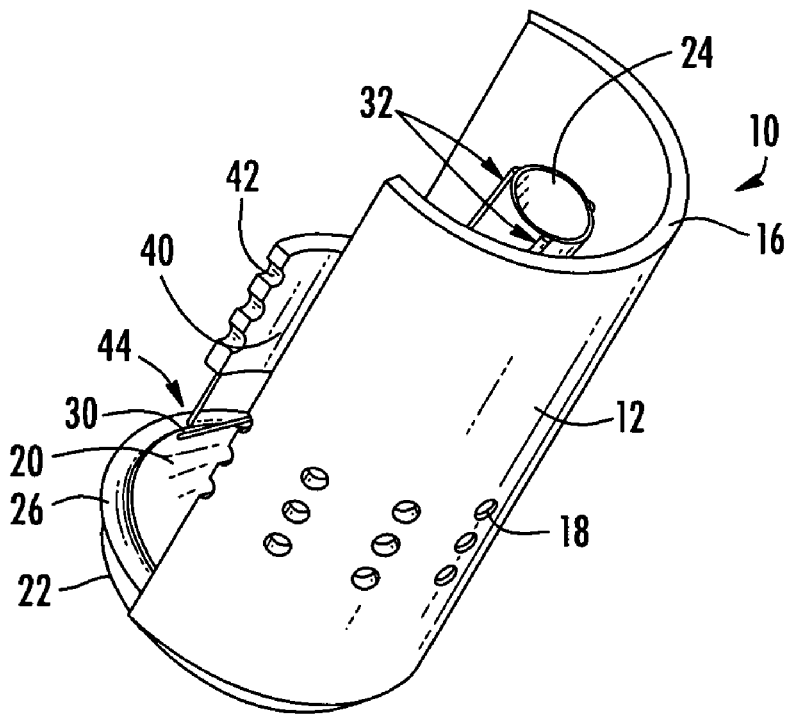

FIGS. 2A and 2B illustrate the variable positioning of adaptive nozzle 20 within outer tube 12. FIG. 2A shows adaptive nozzle 20 in its original undeflected state when actuators 30 (not seen in FIG. 2A) and 32 are turned off. FIG. 2B shows adaptive nozzle 20 in a deflected configuration resulting from activation of one or several of actuators 30 (not seen in FIG. 2B), resulting in constriction of one or two actuators 30, which pull adaptive nozzle 20 toward the position of activated actuators 30. The configuration shown in FIG. 2B, however, leads to a misalignment of the outlet direction, which is no longer coaxial with outer tube 12. To compensate for this effect, actuators 32 are activated, e.g., contracted under controlled heating by an electrical current, which then bend adaptive nozzle 20 such that nozzle tip outlet 24 can be aligned again coaxially with the long-axis of outer tube 12. Thus, this mechanism compensates for the axial misalignment error produced by a deflection of adaptive nozzle 20 and promotes a particle release aligned parallel to the inhalation airflow, thereby avoiding undesirable premature mixing effects and early wall deposition.

With reference now to FIGS. 1, 2A and 2B, smart inhaler device 10 can comprise in some embodiments an inner tube 40 fitted within the interior of outer tube 12 and slidingly engaging the inner surface wall of outer tube 12. Inner tube 40 further comprises air inlet perforations 42 that can align with outer tube air inlet perforations 18. One or more actuators, shown as SMA actuators 44 in FIG. 1, are linked to inner tube 40. When activated SMA actuators 44 can position inner tube 40 such that the alignment of inner tube air inlet perforations 42 are aligned or misaligned to varying degrees with outer tube air inlet perforations 18. By aligning or misaligning inner tube air inlet perforations 42 with outer tube air inlet perforations 18, the inlet cross-section for air flowing into outer tube 12 to create the inhalation airflow can be controlled depending on the measured and computational fluid-particle dynamics "CFPD"-predicted set point inhalation waveform. Thus, regardless of the breath pattern of the subject utilizing smart inhaler device 10, a desired inhalation waveform can be attained.

In some embodiments, wherein SMA actuators 44 operate under tension, an external restoring force (not shown) can be utilized to return inner tube 40 to its original position once actuators 44 are turned off. In some embodiments, the external restoring force is supplied by a spring washer, against which the actuators 44 work.

Figure 3:
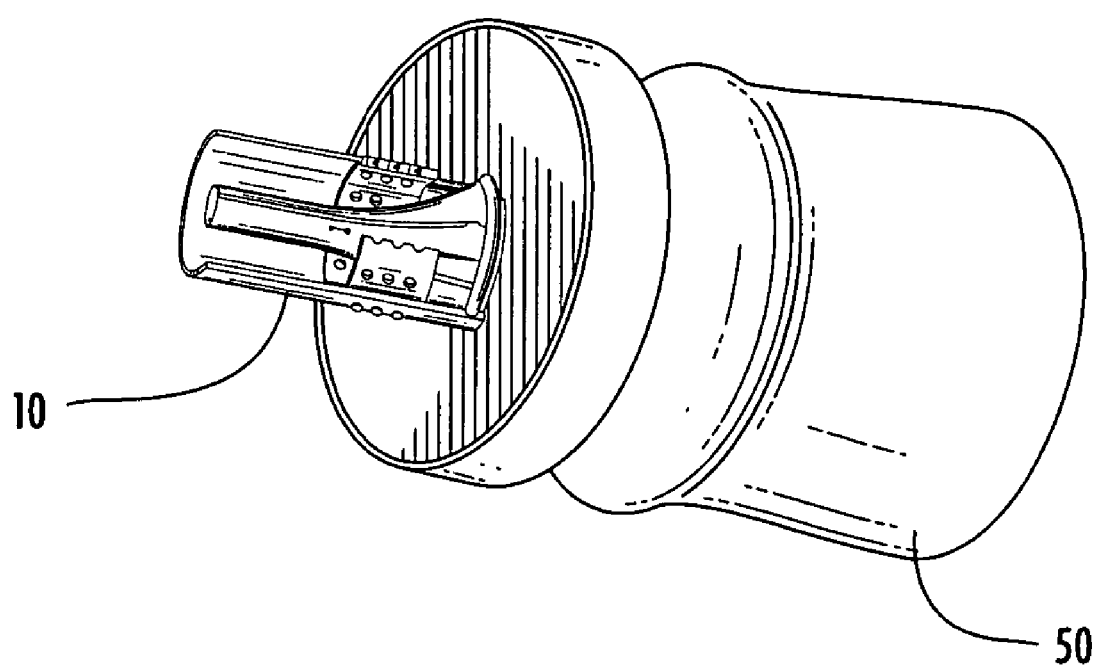
FIG. 3 is a perspective view of one embodiment of an inhaler device and controllable reservoir chamber as disclosed herein.

In some embodiments the smart inhaler system comprises inhaler device 10 in flow communication with an aerosol injection system, which in turn is in flow communication with an aerosol source. In some embodiments, and as illustrated in FIG. 3, the aerosol injection system can comprise a controllable reservoir chamber 50. In some embodiments, controllable reservoir chamber 50, through a system of microsized pressure sensors, such as for example similar pressure sensors as utilized to measure the inhalation waveform, and valves, allows for the transformation of each aerosol source's input into a unified controlled state. The aerosol suspension is then directed through adaptive nozzle 20 at nozzle base inlet 22 and out through nozzle tip outlet 24, where the aerosol stream is injected into the inhalation airflow flowing through the interior of outer tube 12. For example, in some embodiments a microvalve (e.g., a microvalve available from TiNi Alloy, Inc., San Liandro, Calif., U.S.A.) can be incorporated into controllable reservoir 50. In some embodiments the microvalve uses a thin film SMA actuator.

In some embodiments, an inlet microvalve is placed directly at a reservoir inlet, where it controls entry of the aerosol from the aerosol source into controllable reservoir chamber 50. A pressure sensor that measures pressure within controllable reservoir chamber 50 is also placed within active reservoir chamber 50. Depending on the pressure measured by the sensor, reservoir chamber 50 can include an outlet microvalve as well that can open an outlet of active reservoir chamber 50, which connects with nozzle base inlet 22, to maintain the level necessary for optimal aerosol injection into the inhalation airflow.

Figure 4:
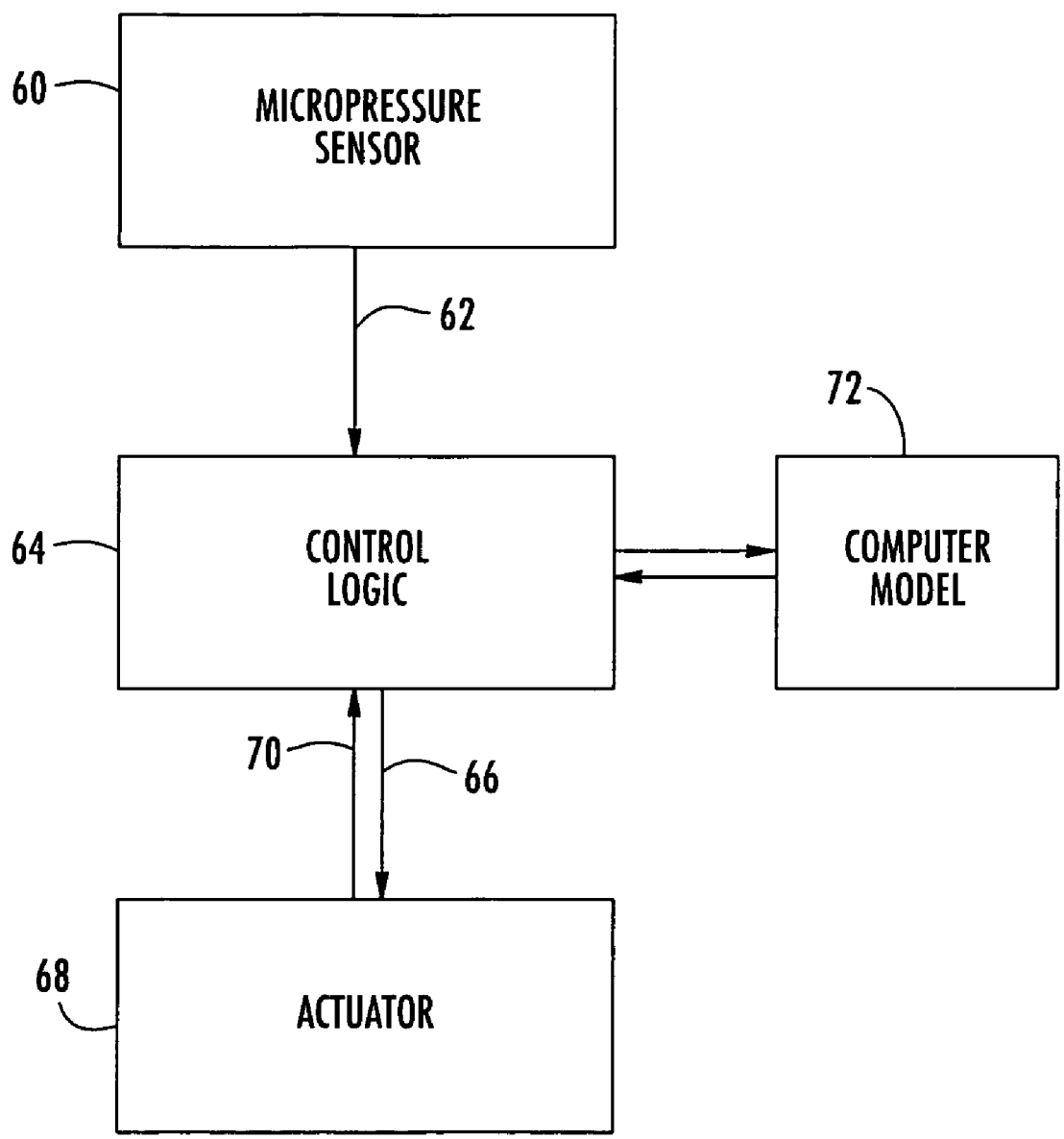
FIG. 4 is a flowchart showing micropressure sensor, control logic, and actuator interactions.

In some embodiments, the presently disclosed smart inhaler system comprises a control logic that interlinks sensor signals with the corresponding actuator outputs. In some embodiments, for example, as can be seen in FIG. 4, a signal 62 from one or more micropressure sensors 60 is transmitted to control logic 64 which interprets signal 62 and transmits an actuator control signal 66 to one or more inner tube actuators 68 which vary the position of inner tube 40 to change the alignment of inner tube air inlet perforations 42 with outer tube air inlet perforations 18, thereby altering the inhalation waveform. In some embodiments, control logic 64 responds to signals not only from the micropressure sensors measuring inhalation waveforms, but also from signals 70 originating either from strain gauges or actuators 68 themselves measuring nozzle or inner tube positioning. For example, SMA actuators, due to changes in resistivity, can also act as sensors, and therefore these data can be used to determine adaptive nozzle 20 and inner tube 40 positions before and after actuator changes.

Further, control logic algorithm 64 can be in operational communication with a computer model for fluid particle flow 72, which provides computational fluid-particle dynamics results that determine one or more of the desired inhalation waveforms and the desired position of adaptive nozzle 20 and therefore prescribes the desired actuator set points to direct the active agent to the target area of the lung of the subject. In some embodiments, the control approach is based on a standard proportional-integral-derivative (PID) algorithm. One of ordinary skill in the art would recognize that other algorithms can be suitable for use with the presently disclosed subject matter, upon a review of the same.

The presently disclosed smart inhaler system through its modular structure can be used in a number of different applications. Such applications include clinical applications, wherein the presently disclosed inhaler system can be integrated into stationary systems. The presently disclosed inhaler system also can be employed for personal use, such as for use in portable asthma systems, for example, when combined with a microprocessor. Such inhaler systems for personal use are feasible through the miniaturization enabled by the use of shape memory alloys.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Disclosed herein are methods and systems for providing "controlled air-particle streams" where most of the drug aerosols reach the desired lung target area (e.g., 45%-92%) based on simulations relying on computational fluid-particle dynamics (CFPD) techniques. The methods and systems were successfully tested for microparticle targeting on a hemispherical tumor located in the third lung generation, using a validated computer simulation model including consideration of optimal particle characteristics, mouth release position, and air/particle velocities (see, for example, Kleinstreuer & Zhang, 2003). Further testing and validation in physical models utilizing embodiments of the smart inhaler system are disclosed in the Examples following.

In brief, a suitable physical replica of the upper portion of a human respiratory system is designed and built, and then the smart inhaler's ability to target specific regions of the lung for particle deposition is quantitatively measured. Although there is variability in exact lung morphology from person to person (based on gender, age, size, etc.) the models built can be representative of a typical lung morphology. The advantage of a tightly coupled computational/experimental approach is that controlled and reproducible experiments can be used to validate the computational models. The computational models can then be used in further assessments to explore the effects of lung morphology variations on particle trajectories and deposition, together with clinical testing.

The lung replica and smart inhaler components are combined to show that individual branches of the simplified lung replica can be targeted. The computer prediction model is used to determine the aerosol release position and inlet flow conditions, the nozzle system is used to adjust to the predicted position, and a laser detection system measures aerosol concentration in each of the individual outlets to verify the ability to target individual branches in agreement with the model predictions.

The local deposition efficiency is also validated. To this end, the focus can be on one particular branch of the system, in which an artificial tumor of varying size is placed. The aerosol deposition on the artificial tumor is then predicted and measured.

Example 1

Model Smart Inhaler System Utilizing SMA Actuation

The results of the CFPD simulations described herein illustrate the importance of particle characteristics, the location of particle release, and controlled inhalation waveform. Starting with the concept of optimal particle release position, it has been combined with the advantages offered by shape memory alloys (SMA) as disclosed herein in order to design a smart inhaler device. The particle release at a controlled position is enabled in some embodiments by a shape memory actuated flexible adaptive nozzle. FIGS. 1, 2A and 2B illustrate the concept of the design, showing the nozzle, which can be deflected by three SMA wires in order to move the nozzle tip to an arbitrary position in the outer tube outlet cross section. The nozzle base is connected to the outer tube by an O-ring, providing sealing functionality and flexibility at the same time. A second set of SMA wires is incorporated into the nozzle and aligned along its long axis. This set of wires can bend the nozzle when contracted under controlled heating by an electric current, and can thus compensate for the axial misalignment error produced by the nozzle tip deflection. This combination assures an aligned particle release, avoiding undesirable mixing effects in this phase of the process.

A third set of SMA wires moves the perforated inner tube with respect to the fixed outer tube in order to adjust the inlet breath air. This part of the system can be used to control the inlet air.

The design of the adaptive nozzle, is facilitated by extensive simulation in order to determine suitable geometry, stiffness, and in particular, optimal actuator placement. A very efficient SMA model has been developed, which includes an energy balance for full thermo-mechanical coupling, and therefore is particularly suited for the description of SMA actuators. The model has been further extended to apply to other active materials actuators like piezoceramics (Smith et al., 2003) and magnetostrictives (Smith et al., 2003) as well. The model provides guidance for real-time optimal control for SMA actuators. (Mueller & Achenbach, 1985; Mueller & Achenbach, 1989; Seelecke, 1999; Seelecke & Papenfuss, 1999; Seelecke et al. 2001).

For the purpose of structural simulation, a finite element formulation of this model has been developed and successfully implemented into the commercial finite element code ANSYS (Seelecke & Papenfuss, 2000, Frautschi & Seelecke, 2003). Although there is a relatively small number of other FE implementations of SMA models published in the art, these are purely isothermal, focusing on the reproduction of uncontrolled processes and thus do not allow to simulate the behavior of a structure with a SMA actuator. An overview of simulation and controls aspects of SMA actuators in smart systems is disclosed in the review article of Seelecke & Mueller (2004), which is incorporated herein by reference in its entirety.

To guide the design process, a series of finite element simulations can be performed. ANSYS can be used as a platform, which allows for geometry import from the 3D solid modeling program used for the smart inhaler system design. The adaptive nozzle can be modeled by appropriate shell elements, and for the SMA wires the FE implementation of a version of the Mueller-Achenbach model can be used. This combination allows for a realistic determination of the time-dependent nozzle deflection together with the necessary forces and related energy consumption.

The open loop behavior of several embodiments of the adaptive nozzle can also be investigated. Specifically, the (x,y)-displacement of the nozzle tip in the plane of the outer tube outlet cross section can be measured. Non-contact laser sensors and camera-based methods can be utilized for this purpose. The above measurements can be performed on different embodiments of the adaptive nozzle in order to provide feedback for improvement of both simulations and prototype building.

Figure 5:
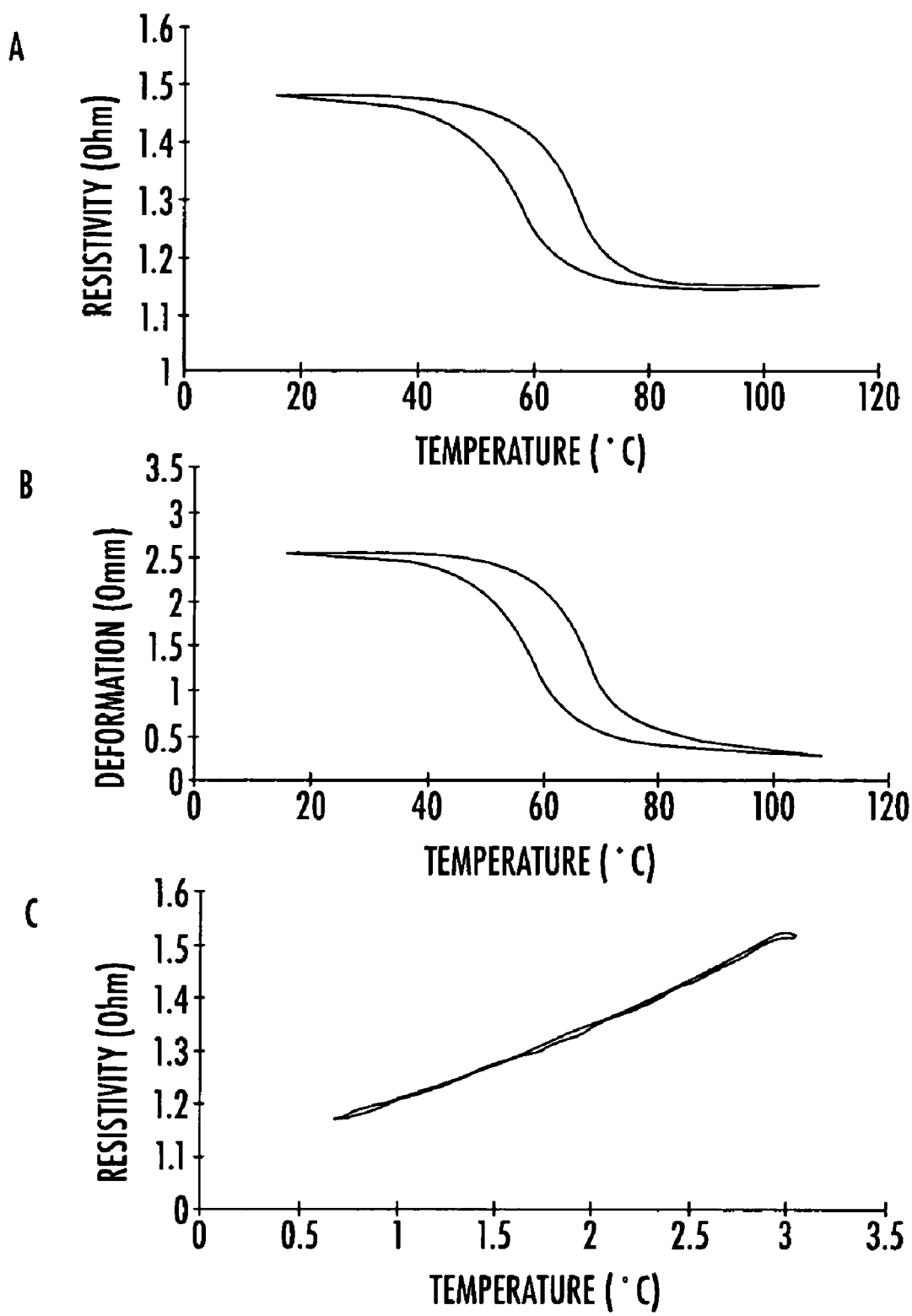
FIGS. 5A-5C are graphs showing sensor properties of SMA materials based on deformation-resistivity relations.

Further, the sensor capabilities of the SMA materials can be investigated at the same time. In addition to the actuator properties due to the temperature-induced contraction, the SMA wires also exhibit a change in electrical resistivity (see FIG. 5B). This can be used for sensing purposes, making the material truly multi-functional. A plot of deformation vs. resistivity reveals that the hysteresis can be eliminated, yielding a unique relation between stroke and resistivity. See FIG. 5C. This feature has received relatively little attention in the art so far except for, e.g., Pitschellis (1998), but it is inherently attractive for the simple reason that there is no need for an additional sensor to determine nozzle and inner tube positions. This becomes particularly important as the non-contact sensors used for initial evaluation can be too big to be incorporated in a miniature system, and other types of devices introduce additional complexity.

A device was constructed to develop and verify the algorithms disclosed herein. It comprises an electrically driven SMA wire connected to an elastic cantilevered steel beam. The device can be filled with a fluid in order to achieve higher frequencies due to the improved cooling.

Example 2

Verification of CFPD Predictions and Smart Inhaler System

The experimental model of the human respiratory system utilized for laboratory testing of the smart inhaler system can include highly detailed oral airways, pharynx, larynx, and trachea for verification of the CFPD predictions and smart inhaler. The flow from the trachea can be divided, non-equally, into the left (~40%) and right (~60%) primary bronchi. Attached to the right primary bronchus can be a four-generation planar upper bronchi section or a fully three-dimensional upper bronchi section. This laboratory model permits the measurement of flow characteristics and particle depositions.

To accurately simulate various modes of breathing, a sophisticated airflow delivery system can be constructed to generate a wide range of inhalation profiles, permitting the investigation of profiles from rest breathing to hypernea. In the following sections, the three different sections of the laboratory lung model are described in detail, followed by a description of the existing airflow delivery system. A brief overview of the diagnostic tools to be employed for the measurement of velocity profiles and particle depositions is also included.

The experimental investigations can be tightly coupled with the computations and development of the smart inhaler. An objective of the experimental measurements is to confirm the ability of the smart inhaler to control the trajectory, and hence the deposition location of the drug aerosols. One exemplary measurement of significance in the present Example is the particle flux through each of the sixteen bronchi exits. Particle flux measurements can be used to validate the computational code. Once the computational code is validated for various breathing modes, without the smart inhaler, the inhaler can be added to the geometry. Using the CFD code to guide the smart inhaler deflection, particle flux measurements can be made to validate the smart inhaler's ability to control the placement of pharmaceutical agents.

Construction of an Airflow and Microparticle Delivery System.

Supplying the smart inhaler, and hence the human upper airways, is a precisely regulated and filtered airflow system. The upper bronchi models can be incased in an air-tight vessel, upon which a vacuum can be pulled. A calibrated mass flow meter can be used to control the airflow rate into the oral and/or nasal cavity, nominally 10 to 60 standard liters per minute. Between the air tight vessel and the mass flow meters, the airflow can enter into a large plenum. Mounted on two sides of this plenum are large-diameter, solid-cone loudspeakers that are driven by an amplified frequency generator. The loudspeakers act as pistons, and the resulting boundary movement causes a variation in the conducting zone inlet flow rate.

Thus, an average mass flux can be maintained with a prescribed oscillation superimposed upon the flow to simulate the time-dependant nature of actual inhalation modes, e.g., normal, pathological, light and heavy exercise. This oscillation has been shown to affect particle deposition in the airway (Finlay and Gehmlich, 2000). A high wattage, solid cone loudspeaker driven with a reasonable amplifier is sufficient to mimic the 3-5 mm Hg intrapulmonary pressure experienced in the lungs.

To better simulate human breathing, a voltage-time profile can be generated on a PC supplied to the loudspeakers via an analog I/O board and linear amplifier. Using a PC with LABVIEW® software (National Instruments Corp, Austin, Tex., U.S.A.), virtually any breathing mode can be simulated. If the loud speakers are not sufficient to generate desired, a linear motor with feedback control can be utilized instead. Loud speakers are capable of developing small pressure differentials, whereas a linear motor is capable of generating 100 kPa of pressure, with millisecond time response.

Construction of Human Airways Replica and Airflow Measurement.

Based on the measured geometric shape of the human oral/nasal passage from actual castings of adult human airways (Cheng et al., 1999), a rigid passageway can be constructed of plexiglass cross-sections, which mimics the actual upper conducting zone very accurately. By seeding the inlet airflow with monodispersed particles, particle-size-dependant fluxes throughout the upper conducting zone can be measured. Constructing the Inlet to Trachea Outlet submodel of stacked cross-sectional pieces allows the model to be sectionalized and permit the exit velocity profile to be measured at any location in the submodel by removing the downstream sections (this can be done via Particle Image Velocimetry and used to validate the computational code). This can allow proper velocity field characterization at three (or more) locations: the entrance to the pharynx; the entrance to the larynx; and the exit of the upper trachea.

By using a planar velocity measurement technique that is able to collect the entire flow field instantaneously, time resolved velocity measurements can be made as a function of the temporal location within the prescribed inhalation mode. Particle flux measurements can also be made simultaneously with the velocity measurements. By assuring a uniform particle seeding density at the inlet to this submodel, particle flux measurements downstream of the inlet can provide information on the particle dynamics and transport through the airways of the upper conducting zone.

If the particles inhaled are not monodisperse, which is true of all real therapeutic drug aerosols, then it can be desirable to understand the possible effects of particle size on transport through the mouth, larynx, and trachea and into the lung.

To model this effect accurately, experimental validation of computational codes can be performed. This Mouth-Trachea submodel can be an ideal code validation tool. Monodisperse particle densities can be determined at the same time that the velocity field is measured, using particle image velocimetry (PIV). However, to measure the density of a polydisperse particle field, particle sizing must be done. This can be accomplished with point measurements using a laser scattering interferometer. The entire field does not need to be mapped; the regions of particular interest can be identified from the planar particle density measurements obtained from the PIV measurements.

Additional submodels utilized can be experimental devices that allow the measurement of particle fluxes through the bronchi. An upper bronchi model can be planar in geometry with symmetric bifurcations, corresponding to the Weibel distributions. A fully three-dimensional lung model that contains four generations of bifurcations after the first split between right and left primary bronchus can also be constructed. The right primary bronchus can be developed into the subsequent generations due to its larger volumetric flow rate and the fact that particle deposition is more likely in this bronchus due to its more vertical position. The left primary bronchus and the sixteen bronchi outlets can each be exposed to the sub-atmospheric pressures generated in the air-tight volume.

The planar symmetric model can be constructed with glass tubes, allowing visualization of particle deposition. The diameter of each tube throughout the four generations can be based on the measurements of Weibel (1963). The initial diameter, representing the trachea, can be 18 mm, with an unsymmetrical initial bifurcation into the left and right primary bronchus. The right primary bronchus can have a diameter of 12.2 mm. All succeeding bifurcations can be symmetric, with a final tube diameter of 3.5 mm.

The more realistic upper bronchi model can be fully three-dimensional and asymmetric. Out-of-plane effects can be quantifiable by varying the degree of departure from two-dimensional in the various generations.

Diagnostic Tools to be Employed.

Particle Image Velocimetry (PIV) is a planar velocity measurement technique that provides nearly instantaneous velocity fields. The technique employs multiple scatterings of laser light off seed particles. In one PIV technique, the second harmonic radiation (532 nm) from a pair of Nd:YAG lasers is formed into sheets of light which are overlapped in space and offset in time by an adjustable amount. The two Nd:YAG lasers are housed in a single laser head, facilitating alignment.

Each Nd:YAG laser is capable of producing 25 millijoule (mJ) in the green in a 8 nanosecond (ns) pulse. The scattered laser light is captured on a Kodak large array (1K by 1K) digital interline transfer camera, specifically designed for PIV measurements. With this experimental setup, the first laser pulse scatters light off seeded hollow spheres and is captured by the digital camera located normal to the sheet. The camera stores this image on the chip and then captures the second laser pulse, which is delayed from a few to a few hundred microseconds, depending upon the mean velocity. The image pair is then downloaded and a cross correlation technique is used to match up particle pairs, which then yield velocity vectors. The advantage of PIV over other velocity measurement techniques is that it measures the entire planar velocity field nearly instantaneously. The advantage of this particular experimental setup is that there is no velocity ambiguity and stagnation flows are resolvable.

The particle flux measurements can be made by Mie scattering laser light off the particles as they exit the bronchi tube. This scattered light can be collected via a lens-coupled photomultiplier tube. The intensity of the scattered light can be a quantitative measure of the number of particles passing through the laser probe volume. This is a time resolved measurement and allows the particle flux to be measured throughout the inhalation cycle. This quantitative information can provide validation of the computational code.

Example 3

Computational Fluid-Particle Dynamics (CFPD) Simulations of the Human Respiratory System and Smart Inhaler Outer Tube Outlet Conditions One goal of the CFPD analysis is to provide particle characteristics and air-particle flow data sets which lead to a smart inhaler system for substantially maximum drug delivery. This can be facilitated by the accurate simulation of air-particle flow in representative human airway models. With the experimentally validated computer simulation model, optimal inhaler outlet conditions equal to the desired mouth inlet conditions can be determined for both the laboratory replica and representative upper airway configurations. The fluid-particle dynamics inside the inhaler system, including possible aerosol deposition, can be more effectively visualized and measured, via a segmental mass balance, in the laboratory.

Airflow and Airway Wall Structure Equations.

In order to capture the isothermal airflow pattern in realistic upper lung airways and to check for possibly transitional airflow, i.e., the laminar-to-turbulent flow regimes, the low-Reynolds-number (LRN) k-$\omega$ model of Wilcox (1998) has been selected and adapted. It has been demonstrated that the modified LRN k-$\omega$ model is appropriate for such internal flows (Zhang & Kleinstreuer, 2003a). All air transport equations, including the heat transfer equation, as well as initial and boundary conditions are given in Zhang & Kleinstreuer (2003a, b) and Kleinstreuer & Zhang (2003), each of which is incorporated by reference herein in their entireties.

As part of these Examples, different types of inhalation conditions, especially particle size, particle density, particle release position, and inhalation waveform, can be considered. The laboratory airway replicas including oral cavity, pharynx, larynx and tracheobronchial airways, as provided herein, can be used to generate meshes for the air-particle flow simulations. In addition three different airway cast models can be selected to give information to investigate inter-subject variations. The boundary conditions for different surface and wall configurations, e.g., roughness effects, cartilageous rings, mucus film etc., including constant or variable temperature conditions (cf. Daviskas et al., 1990; Morris, 1988; among others) can be implemented. The optimal fluid-particle stream and maximum aerosol deposition analyses can provide the actual inhaler air-particle exit conditions and can be used in the laboratory as mouth inlet conditions.

The airway wall structure equations utilized are the standard conditions of equilibrium, stress-strain relations, and conditions of compatibility (see, for example, Ugural & Fenster, 1995 or Fung, 1994). Wall material properties and airway expansion measurements are given in Fung (1981) and Kamm (1999). Computational fluid-structure interaction simulations can be readily implemented.

See Zhang et al. (J. Aerosol Science (2005), vol. 36, pp. 211-233) for governing transport equations, boundary conditions, and solution procedure, including computer model validations.

The numerical solutions of the continuity, momentum, and turbulence transport equations, along with scalar advection equations can be carried out with a parallelized finite-volume based code (CFPD code), which was developed especially for laminar-transitional-turbulent flows in bio-fluid applications. The numerical program uses a structured, multiblock, body-fitted coordinate discretization scheme. The complex meshes are generated with GRIDPRO® (PDC, White Plains, N.Y., U.S.A.). High-resolution upwinding techniques can be used to model the advective terms of the transport equations. To achieve higher-order spatial accuracy, interface flux reconstruction can be performed using either second order total variation—diminishing (TVD) or third order (fifth order in smooth regions) weighted essentially non-oscillatory (WENO) interpolations of the solution variables. Any inhalation waveform can be accommodated, including aerosol inhaler outlet conditions.

The particle transport equations can be solved with an off-line F90 code with parallelized algorithms (Longest et al., 2004).

Airway Geometries.

The airway geometries can include the oral cavity, pharynx, larynx, trachea, and 13 generations of bronchi (G0-G12). Comparisons of the deposition efficiencies between the numerical simulations and experimental observations (i.e., mouth to G-9) can be made to verify the computer model. Once the validity of the numerical technique is established, the numerical simulation of the conducting airway can be extended to generation 12 (G12), considering both symmetric Weibel configurations for ease of model validation and international data transfer as well as asymmetric configurations as tabulated by Raabe et al. (1976), Horsefield et al. (1971), and Ley et al. (2002), among others. Geometric variations can also be included for double and triple bifurcations (cf. Corner et al., 2001 a, b; Zhang & Kleinstreuer, 2002; Zhang et al., 2001).

Additional airway features to be considered include cartilaginous rings, especially in the trachea, shape and openings of vocal folds, and movement of liquid (mucus) layers. The simulations of airflow and particle deposition in parallel and series with triple-bifurcation unit are proposed to consider as completely as possible the geometric effects due to intra- and inter-subject variability, particle characteristics as well as inlet conditions obtained from the exit of inhalers or the upstream airway units. Clearly, particles which make it past G12 deposit either in the alveolar region or are being exhaled.

Determination of Optimal Inhaler Outlet Conditions.

Appropriate particle-release locations and timing, suitable particle characteristics, and an ideal inhalation waveform can transport drug aerosols, on a case-by-case basis, to desired lung target areas. FIG. 6 shows the present methodology in virtual reality for normal vs. controlled micro-particle releases from Generation 3 and the mouth via a back-tracking method (disclosed in detail hereinbelow). Specifically, in selecting micro-particles, i.e., $5 \leq d_p \leq 7$ μm, and strictly laminar flow, quasi-deterministic particle trajectories can be achieved; hence, airway landing area and particle release position at the aerosol delivery entrance correlated directly.

FIG. 6 (top) shows the example of a tumor located in generation G2, which under currently used, uncontrolled inhalation conditions (homogenized throughout mouth inlet cross section) receives only a minute fraction of the inhaled aerosol. Utilizing the presently disclosed computations for targeted delivery, it is shown that as a result of a localized particle release within the mouth inlet cross section a) the undesired particle deposition along the airway walls is basically eliminated, and b) the fraction of particles depositing on the tumor is drastically increased (FIG. 6, bottom).

In reality, variations in lung morphology, breathing mode, particle size, and specific lung target area for drug aerosol deposition complicate the task of achieving a controlled air-particle stream which results in optimal drug aerosol deposition. These variations can be addressed, at least in part, by considering the following exemplary criteria:

(a) broadening the particle release area;
(b) selecting the best particle characteristics; and
(c) determining an optimal inhalation waveform.

Figure 7:
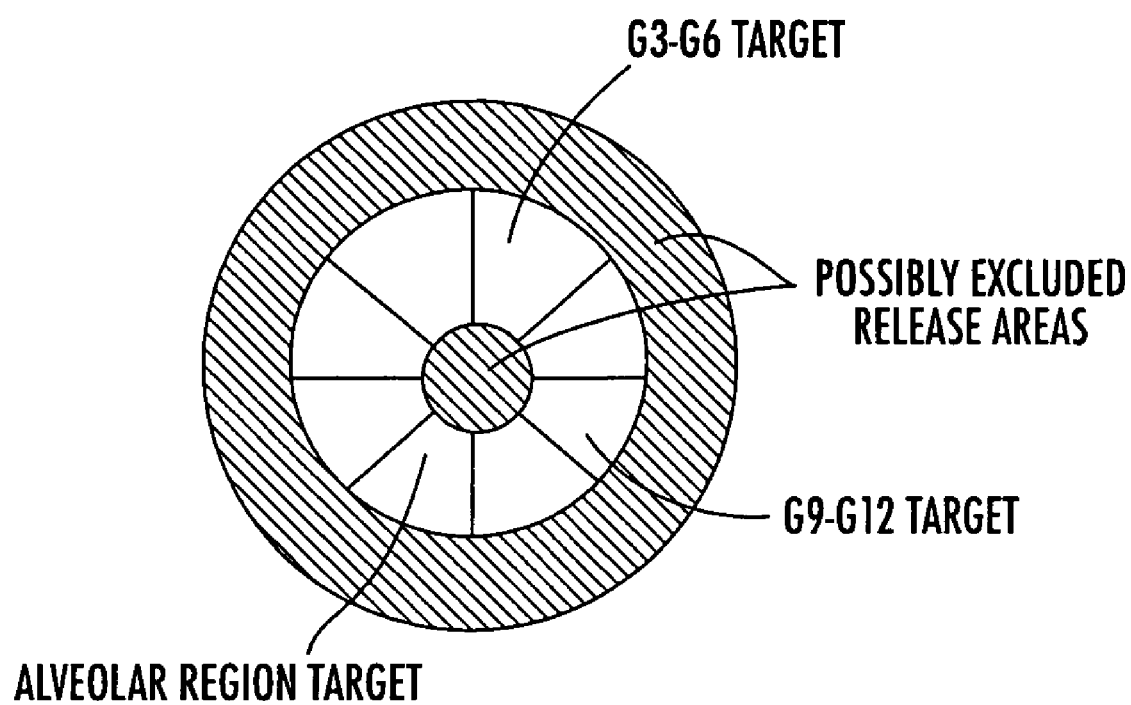
FIG. 7 is a schematic diagram showing examples of nozzle tip outlet particle release positions in inhaler exit plane.

In order to accommodate different airway geometries, e.g., children, adults, the elderly, and to be able to target different desirable lung areas, the mouthpiece cross section (outer tube outlet) can be, for example, divided into eight particle release sections that allow for targeting of, for example, G3-G6 or G9-G12 independently (see FIG. 7). Alternatively, or in combination, "critical radii" can be utilized, as disclosed hereinbelow, to position aerosol stream release. The back-tracking methodology as well as trial and error runs can match the optimal release segment with maximum deposition in the predetermined target region. Some well-defined particle release areas (see FIG. 7, striped regions) can be always excluded because aerosols from such locations deposit typically in the oral airway.

To address (b), the correct effective diameter and density of (probably solid spherical) micro-particles can be determined to achieve the goal of maximum drug aerosol deposition.

Regarding (c), any active or passive inhalation waveform generated by a patient or an existing device (pMDI, DPI, or SMI) can be modified. Specifically, a laminar flow, $Q_{in} \leq 15$ L/min, and a rectangular, i.e., uniform) inhalation waveform can be objectives to generate the highest deposition results.

In summary, the exit conditions of a smart inhaler system can be determined, which, for example, could be attached to off-the-shelf inhalers. A smart inhaler system disclosed herein can ultimately: (i) modify a given waveform (or air stream) to an ideal, e.g., uniform and strictly laminar, waveform, and (ii) direct and concentrate the drug aerosol stream to the test release section (FIGS. 6 and 7) in order to achieve maximum deposition in the desired lung target area.

Example 4

Demonstrated Targeted Delivery of Particles Utilizing The Smart Inhaler System

An objective of the present Example is to fabricate a smart inhaler system disclosed herein and to set up an experimental facility to validate in the laboratory the computer simulations. For this purpose, a replica of the human lung, comprising a glass model, which starts from the oral airways, and continues all the way to the fifth generation lung structure was constructed. The smart inhaler system was implemented into this glass model, and laser-based Mie scattering imagery was used to visualize the particles at various outlets.

In the first phase of the present Example, attention was confined to the steady case, where a continuous air stream was directed through a "lung box", to which various components of a glass model of the airway system can be attached. In order to track the potential dispersion of injected particles with the travel distance, several straight glass tubes of various lengths were used (5 cm, 15 cm, and 20 cm), along with a 90-degree-bend and a 1:1 model of the human oral airway system. Particles are injected initially through a small seeding tube in the outlet cross-section of the lung box. The tube can be placed at any desired or arbitrary position in the cross section.

A laser sheet is then formed at the outlet cross-section of the various components, and Mie scattering provides an instantaneous image of the particle locations. The above system was used initially to optimize the set up of the laser system and image acquisition, along with the seeding system for the particles. Initially, spherical particles obtained from the burning of incense with a nominal diameter of 0.6 μm used. A new seeding system, yielding a wide range of sizes and distributions can be used to accurately simulate a wide variety of pharmaceutical agents. For example, polystyrene spheres of various diameters can be utilized.

In a second phase of the present Example, the initial seeding system was then replaced by a nozzle injector, which had been fabricated using rapid prototyping technology. This first nozzle generation features a static, yet deformed shape, such that the outlet cross section is off-center. Rotation of the nozzle allows adjusting to several different release locations along the perimeter of a circle. Results of the computer-modeling simulations and laboratory experiments are disclosed as follows.

Laboratory Experiments

The first objective is to show that particles do not disperse over the entire airway cross section, but rather stay confined so that they can potentially be directed to desired deposition areas. The second objective is to show that variations in the release position have a deterministic effect on the trajectory of these particles such that their deposition area can in effect be predicted.

For this purpose, stationary experiments were performed at various airflow rates ranging from 40 standard liters per minute (slpm) down to 8 slpm. The injection of the particles was velocity matched to this co-flow to minimize the effect of shear layers, which are expected to lead to premature dispersion. At higher flow rates, transition to turbulent flow can occur which also leads to undesired dispersion.

For each flow rate the particle behavior was studied for a variety of glass pipes of different length in order to document the amount of dispersion as a function of the travel distance. A portion of the large body of results are disclosed below.

When particle injection occurs at a "top" region of the inlet cross section for an air flow rate of 12 slpm, after 20 cm through a straight pipe, the particles are still very close together, and almost no dispersion was observed. After a 90-degree bend, the particles were slightly driven to the outside due to the action of centrifugal forces, but they were still very coherent. After the particles had traveled roughly 40 cm and passed several cross-section variations, a flattened shape was observed. However, it is noteworthy that the particles were still coherent and had not dispersed over the cross-section at all.

The flow rate of 12 slpm also represents the case where the peak Reynolds number exceeds the value of 1800 in the larynx, potentially causing transition to turbulent flow in the trachea.

A similar trend was observed for the case of release at a "bottom" region of the inlet cross-section. Here, the particles stayed even closer together. It is worth noting that it was possible to not only prevent dispersion of particles, but importantly, to also control the trajectory of the particles even over great distances downstream through the choice of release location.

Computer-Modeling Simulations

The results from the laboratory experiments confirmed the general feasibility of the method. Further implementations can utilize predictions from numerical simulations to increase the accuracy of targeted-delivery. Exemplary calculations were run with the CFD code CFX-4 and an in-house particle tracking code, and results for the 8 slpm case are disclosed below.

Figure 8:
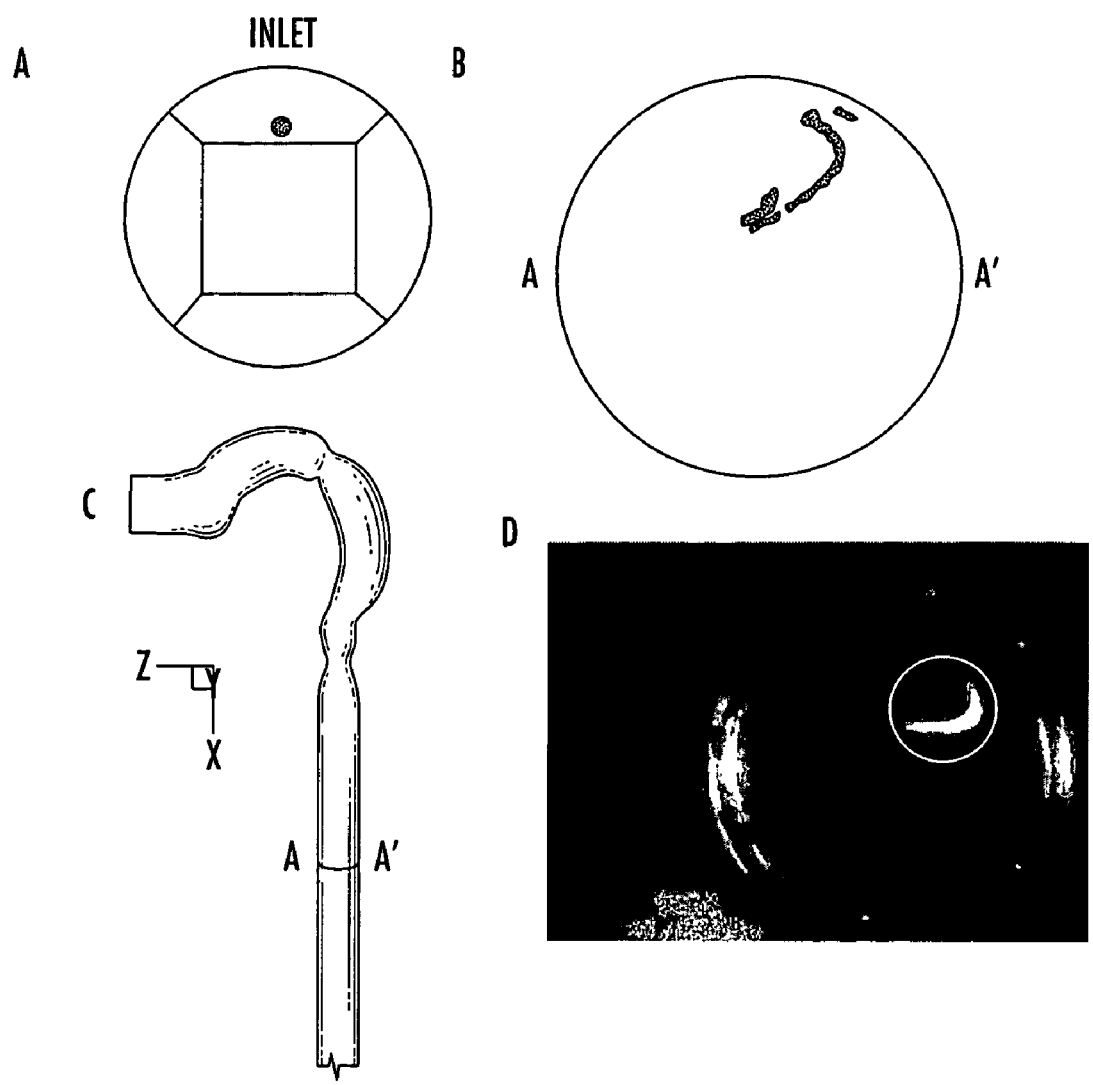
FIGS. 8A-8D are diagrams (FIGS. 8A-8C) and a photograph (FIG. 8D) showing simulation of particle location at outlet cross section A-A' for oral airway geometry, airflow rate of 8 standard liters per minute (slpm), and a release location at "top" (FIG. 8A). Experimental results confirming simulation predictions are shown in FIG. 8D. The circle in the photograph of FIG. 8D indicates measured particle locations.
Figure 9:
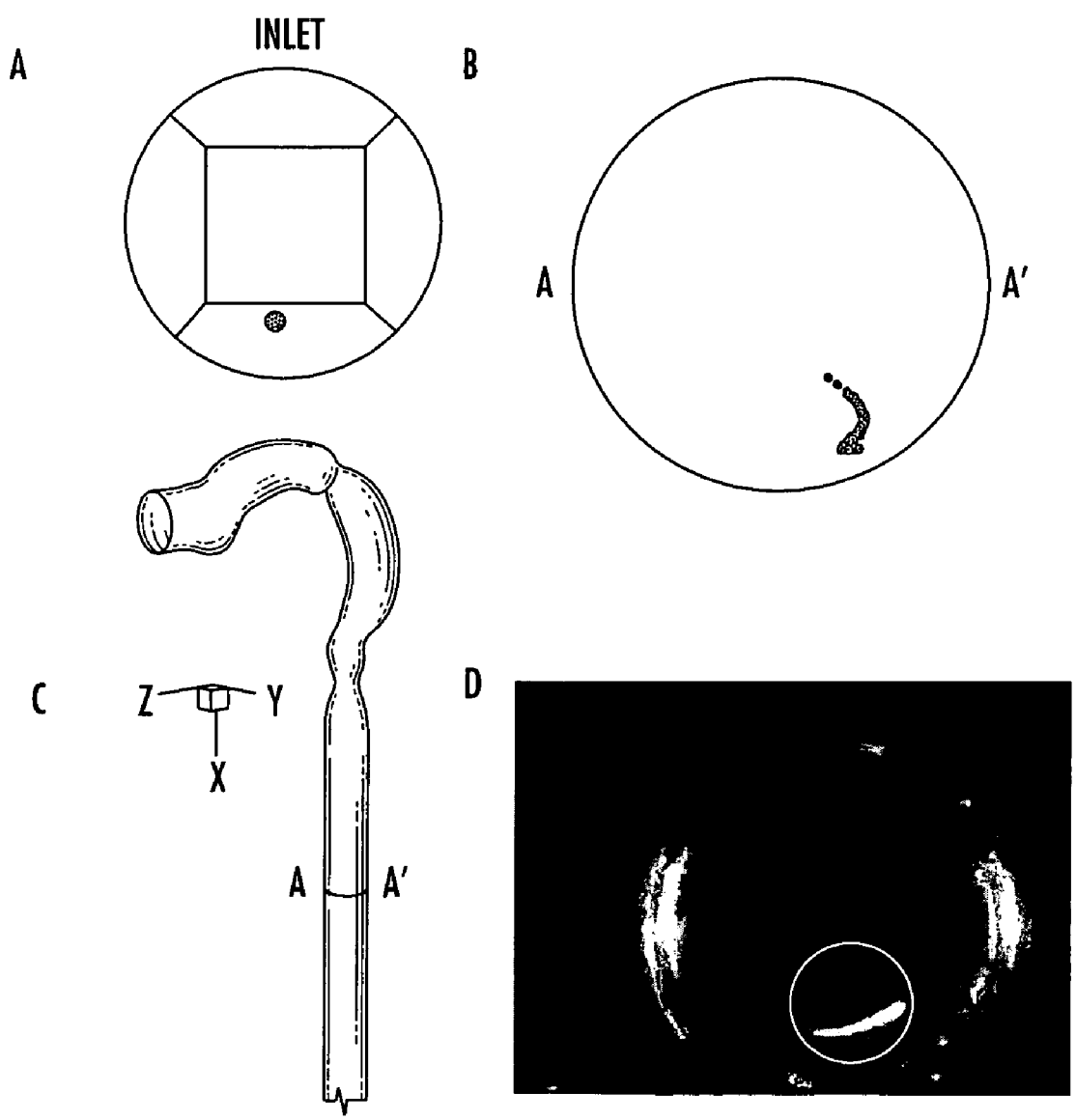
FIGS. 9A-9D are diagrams (FIGS. 9A-9C) and a photograph (FIG. 9D) showing simulation of particle location at outlet cross section A-A' for oral airway geometry, airflow rate of 8 slpm, and a release location at "bottom" (FIG. 9A). Experimental results confirming simulation predictions are shown in FIG. 9D. The circle in the photograph of FIG. 9D indicates measured particle locations.

The comparisons between the simulated and measured particle distributions with different inlet release positions for the oral airway model are shown in FIGS. 8 and 9, assuming a steady inspiratory flow rate of 8 slpm and a spherical particle diameter of 1 µm. 1000 particles were released at the oral inlet. In a comparison of the simulated results for top and bottom release shown in FIGS. 8B and 9B, respectively, with the experimental results for top and bottom release shown in FIGS. 8D and 9D, respectively, the simulated particle distributions agree well with the experimental visualizations.

Figure 11:
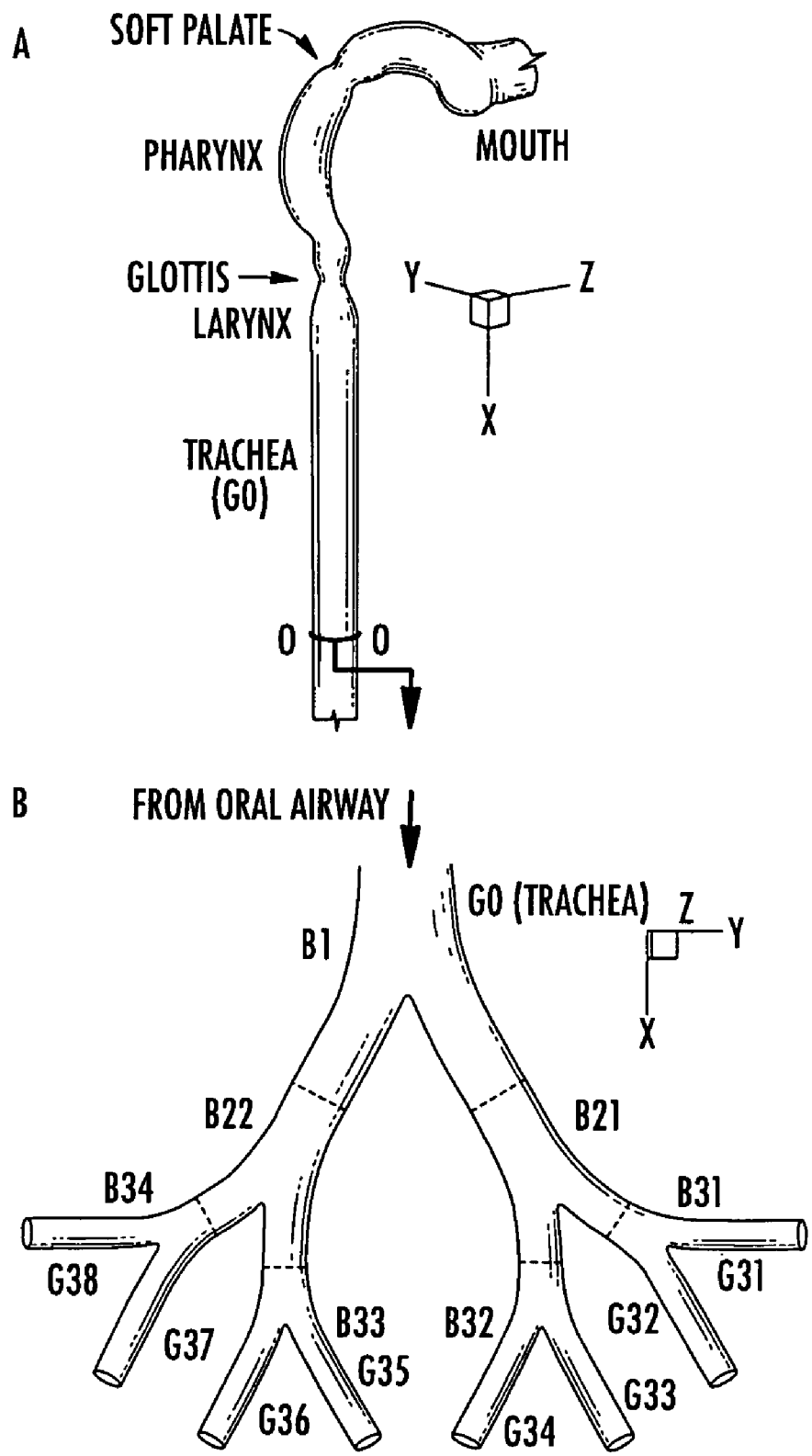
FIGS. 11A and 11B are diagrams showing 3-D views of the oral airway model (FIG. 11A) and bifurcation airway model, Generations G0 to G3 (FIG. 11B). B1—first bifurcation, B21 and B22—second bifurcation, B31, B32, B33 and B34—third bifurcation. The dashed lines indicate the segmental boundaries.

This effect becomes even clearer for the case of the oral airway model with the first bifurcation attached to it (B1 of FIG. 11). FIGS. 10A-10C compare three cases, which differ only by the angular position of the nozzle in the mouth inlet cross section (FIG. 10A). In the left column of FIGS. 10A-10C, particles are released at an angle of 60° with the vertical and occur exclusively in the left branch of the first bifurcation as seen in FIG. 10B, while the right column (release at 240°) shows the opposite result as seen in FIG. 10C. The center column documents that this behavior can be finely controlled to the degree that a fraction of the particles occurs in each branch (FIGS. 10B and 10C).

Minor discrepancies may be attributed to: (i) slight differences in inlet release positions between the simulations and experiments; (ii) differences in visualization locations; (iii) differences in the geometries (for example, there is a transition tube in the experimental setup and the airway geometry becomes slightly different after manufacturing); and (iv) the difference in particle size, i.e., particle distributions are sensitive to factors (i) and (ii).

Conclusions

The above results provide convincing evidence that:
1. Particle dispersion can be avoided for laminar flow conditions; and
2. Particle trajectories, and consequently, deposition at targeted sites in the airway system can be controlled by appropriately choosing the aerosol release location.

It is further important to note that the two documented release locations termed "top" and "bottom" have received their names because of the specific orientation of the oral airway system, which is positioned in the horizontal plane in order to simplify the imaging system set up. In a real human lung, however, these would be left and right hand side, respectively, and, hence, the above experiments have also shown that it is clearly possible to target right and left lobe of the lung separately.

Additionally, it can be seen from the results that, as a by-product of the controlled air-particle stream release, wall deposition in the critical oral airway region has been virtually eliminated. This feature can considerably improve targeted deposition efficiency and reduce significantly potential side effects.

In summary, this Example illustrates the capabilities of the smart inhaler system to enable targeted treating of lung cancer as well as a number of other respiratory diseases. A number of additional therapeutic applications, such as insulin for diabetics, inflammation treatments, blood disorders, pain management, chemotherapy, gene manipulation, etc. are also possible utilizing the presently disclosed smart inhaler system.

Example 5

Drug-Aerosol Release Points From Orbits of Critical Radii

As confirmed by experimental visualizations disclosed hereinabove, micro-particle trajectories can be tracked and are controllable under laminar flow conditions. Thus, given suitable air-inhalation waveforms, particle characteristics and particle release positions, the therapeutic aerosols inhaled via a smart inhaler system can reach the targeted lung areas at large mass fractions to effectively combat different diseases. In turn, deposition of aggressive drugs on healthy lung tissue is avoided.

The adaptive nozzle disclosed herein has thus far been utilized in the above Examples to target particle release. In an alternative embodiment, the concept of "orbital point release with critical radii" is introduced and tested with CFPD simulations in the present Example. It is noted, however, that although the orbital point release methodology can be implemented utilizing targeted-release mechanisms other than the adaptive nozzle disclosed herein, the presently disclosed subject matter is not intended to be limited thus, but rather the present subject matter specifically includes implementing the orbital point release methodology utilizing the presently disclosed adaptive nozzle as well as other targeted-delivery mechanisms.

Airway Geometries

An upper airway model (see FIGS. 11A and 11B) comprising an oral airway cast replica and Weibel Type A triple-bifurcation lung airways, representing generations G0 (trachea) to G3, was employed to investigate the inhalation and transport of drug aerosols.

Numerical Method

The airflow and particle transport were simulated with a commercial finite-volume code CFX4 (ANSYS, Inc., Canonsburg, Pa., U.S.A.) and an in-house off-line F90 particle trajectory code. The computations were conducted on an IBM p575 machine with multiple POWER5® processors (IBM, Armonk, N.Y., U.S.A.).

Model Validations

The comparisons between the simulated and measured particle distributions with different inlet release positions for the oral airway model were utilized as disclosed in detail in Example 4 and shown in FIGS. 8-10. Additional computer model validations and relevant applications can be found in Kleinstreuer & Zhang (2003) as well as Zhang et al. (2002f, 2005), each of which is incorporated herein by reference in their entireties.

Back-tracking and Particle Release Positions

The specific inlet positions of aerosols which land on different targeted sites are determined via "back-tracking," and then release-controlled air-particle streams are generated so that most aerosols deposit in the desired lung regions, e.g., inflamed left or right lower airways, etc.

Release positions of particles deposited in the upper airways as well as those which exit airways of generation G3 vary depending in part on particle diameter ($d_p$). Simulations were run with $Q_{in}$=8 L/min and $d_p$=7, 10, or 20 μm. The depositions of particles with $d_p$=7 and 10 μm are minor in the upper airways due to relatively low inertial impaction. Most of them can enter the deeper lung regions. In general, particles released from the left and right sides of the circular mouth entrance enter the left and right lungs, respectively. However, the inlet positions of particles leaving different portions of G3 vary irregularly due to the effects of secondary flows.

If the targeted regions are located in the upper airways, larger-size particles (e.g., 20 μm) can be employed to enhance the deposition when utilizing a low inhalation flow rate (e.g., 8 L/min).

Release from Orbits with Critical Radii

It has been determined, as disclosed herein, that particles released from different fixed regions can enter different parts of the lower airways (i.e., after G3). Targeting can be achieved by calculated positioning and aligning an adaptive nozzle disclosed herein in the inhalation tube for different patients and diseases. Positioning can be potentially simplified by calculated particle release from orbital points, i.e., from circles with critical radii. In this case, a tube-aligned nozzle with adjustable outlet diameters can rotate following the predetermined orbit of a critical radius (see FIG. 12). The nozzle can be positioned at a specific angle (or orbit location) so that most of the released particles can reach the desired areas.

Figure 12:
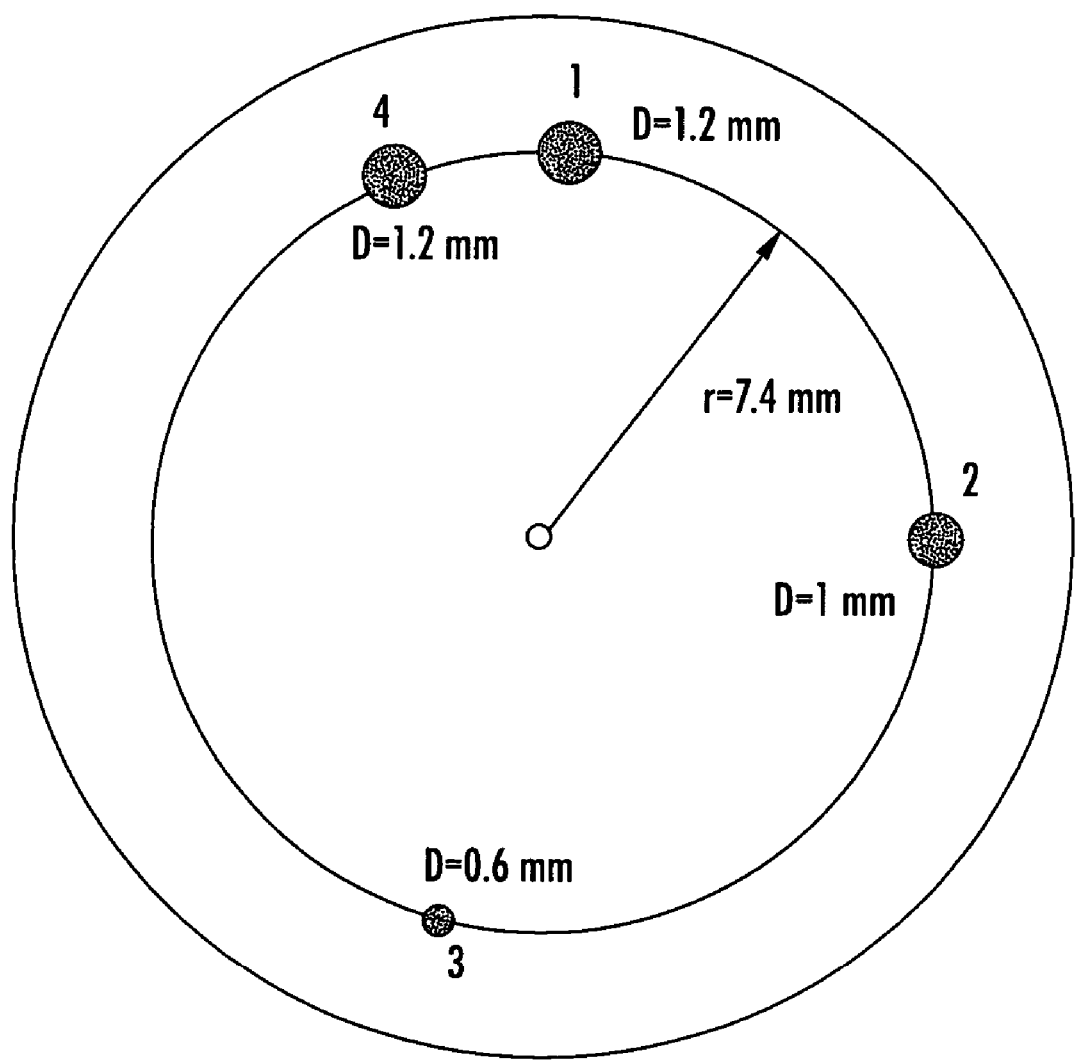
FIG. 12 is a diagram showing particles released within a critical radius.
Figure 13:
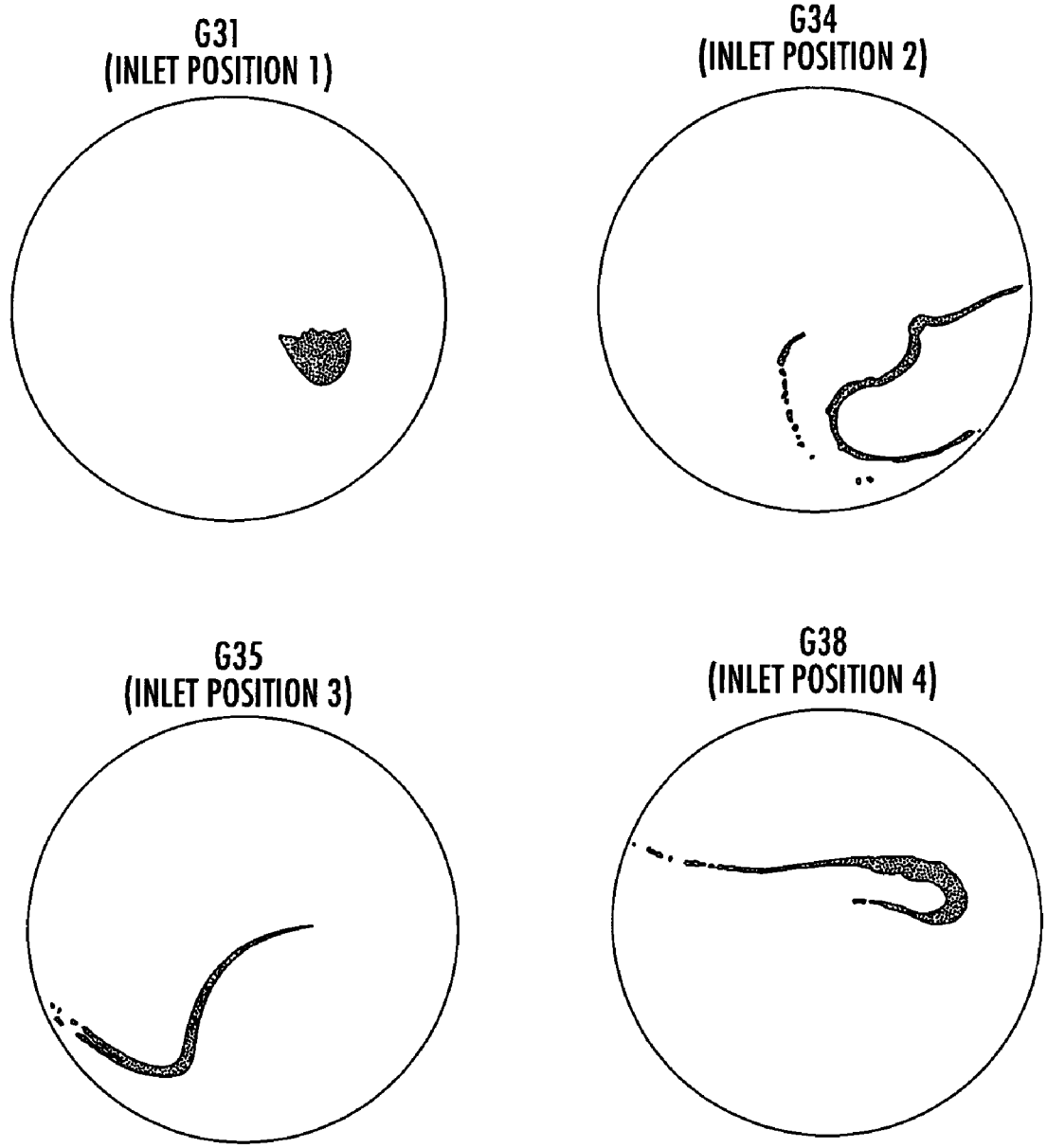
FIG. 13 is a diagram showing distributions of particles leaving different tubes of generation G3 with different given release positions at the mouth inlet ($Q_{in}$=8 L/min and $d_p$=7 μm; dry air).

As an example, the targeted regions for inlet-release positions 1 to 4, as shown in FIG. 12, are the four outlets in the lower airways after generation G3 (see Table 1 and FIG. 13). Particles leaving from G31 and G34 may enter side and central parts of the left lung, respectively, while they transport into side and central portions of the right lung after exiting from G35 and G38 (see FIG. 11). Specifically, with the controlled inlet points, the capture efficiency of particle deposition in the targeted areas can increase from about 10% to 60%-100% (see Table 1).

Distributions of particles entering targeted (outlet) airways are depicted in FIG. 13. Some particle dispersion occurs for Inlet Positions 2 to 4 because of the influence of secondary flows. In contrast, Inlet Position 1 is located in a larger particle release area, reaching the G31 airway outlet without any local dispersion. Dispersion can further be decreased when using drug aerosols with attractive surface charges/properties.

TABLE 1

Regional Percentage of Inhaled Aerosols (%) ($Q_{in}$ = 8 L/min, $d_p$ = 7 μm)

| | | Controlled Inlets Positions | | | |
| | | 1 | 2 | 3 | 4 |
| | | | Targeted area | | |
| Region | Normal Inlet | G31 outlet | G34 outlet | G35 outlet | G38 outlet |
| Deposition in the oral and G0-3 | 2.23 | 0 | 0.22 | 2.09 | 0.08 |
| Exit G31 | 12.36 | 100 | — | — | — |
| Exit G32 | 14.29 | — | — | — | — |
| Exit G33 | 12.48 | — | 35.63 | — | — |
| Exit G34 | 8.93 | — | 64.15 | — | — |
| Exit G35 | 13.23 | — | — | 89.51 | 0.81 |
| Exit G36 | 14.75 | — | — | 8.38 | — |
| Exit G37 | 11.85 | — | — | 0.02 | — |
| Exit G38 | 9.88 | — | — | — | 99.11 |

Nozzle Positioning

As disclosed herein, a specific disease, lung tumor location, and/or suitable treatment determine the desired lung target site or region. Some of these predetermined deposition areas can be reached as demonstrated in FIG. 13 and Table 1. Implementation can be achieved as follows.

A nozzle with variable exit diameter and substantially, or in some cases, perfectly parallel to the inhaler-tube wall rotates and arrests on selected orbits and at orbital points (see FIG. 13, for example). Changes in nozzle exit diameter and orbital positioning can be implemented via various mechanisms. Examples for varying the nozzle exit diameter include SMA ring-wire control near the flexible nozzle tip or mechanical (camera-like) nozzle aperture changes. Examples for orbital positioning include ball-and-spring-loaded disk/ratchet or a precision-gear mechanism. Different radial settings achieve target-specific orbits.

REFERENCES

The references listed below, as well as all references cited in the specification, are incorporated herein by reference to the extent that they supplement, explain, provide a background for, or teach methodology, techniques, and/or compositions employed herein.

Achenbach M and Müller I (1985). Simulation of material behavior of alloys with shape memory. Arch Mech, 37(6), 573-585.

Achenbach M (1989). A model for an alloy with shape memory. Int J Plast, 5, 371-395.

Benard W L, Kahn H, Heuer A H, and Huff M A (1998). Thin-film shape-memory alloy actuated micropumps. Journal of Microelectromechanical Systems, 7(2), 245-251.

Cheng, Y. S., Zhou, Y., & Chen, B. T. (1999). Particle deposition in a cast of human oral airways. *Aerosol Sci. Technol.,* 31, 286-300.

Comer, J. K., & Kleinstreuer, C (1995). A numerical investigation of laminar flow past nonspherical solids and droplets, *Journal of Fluids Engineering—Trans. of ASME* 117, 170-175.

Comer, J. K., Kleinstreuer, C., & Zhang, Z. (2001a). Flow structures and particle deposition patterns in double bifurcation airway models. Part 1. Air flow fields. *Journal of Fluid Mechanics,* 435, 25-54.

Comer, J. K., Kleinstreuer, C., & Kim, C. S. (2001b). Flow structures and particle deposition patterns in double bifurcation airway models. Part 2. Aerosol transport and deposition, *Journal of Fluid Mechanics* 435, 55-80.

Crowder, T. M., Lousy, M. D., Sethuraman, V. V., Smyth, H. D. C., and Hickey, A. J. (2001). An Odyssey in Inhaler Formulation and Design, *Pharmaceutical Technology, July* 2001:99-113.

Daviskas, E., Gonda, I., & Anderson, S. D. (1990). Mathematical modeling of heat and water transport in human respiratory tract, *J. Appl. Physiol.* 69(1), 362-372.

Duerig T, Pelton A, and Stöckel D (1999). An overview of Nitinol medical applications. Mat Sci Eng A, A273-275, 149-160.

Dunbar, C. A., Hickey, A. J., and Holzner, P. (1998) Dispersion and Characterization of Pharmaceutical dry Powder Aerosols, *KONA* 16:7-44.

Edwards, D. A. & Dunbar, C. (2002). Bioengineering of therapeutic aerosols, *Annual Review of Biomedical Engineering*, 4, 93-107.

Finlay, W. H. (2001). *The Mechanics of Inhaled Pharmaceutical Aerosols: An Introduction*. London, UK: Academic Press.

Finlay, W. H., & Stapleton, K. W. (1995). The Effect on Regional Lung Deposition of Coupled Heat and Mass Transfer between Hygroscopic Droplets and their Surrounding Phase. *J. Aerosol Sci.* 26(4), 655-670.

Frautschi, J.; and Seelecke, S. (2003), Finite Element Simulation of Adaptive Aerospace Structures with SMA Actuators, SPIE Smart Structures and Materials 2003, Modeling, Signal Processing, and Control, San Diego, Calif., 2003, to appear.

Hollerbach J M, Hunter I W, and Ballantyne J, (1992) A Comparative Analysis of Actuator Technologies for Robotics, vol. 2. MIT Press, 299-342.

Keller, M. (1999) Innovations and Perspectives of Metered Dose Inhaler in Pulmonary Drug Delivery, *Int'l J. Parm.* 186:81-90

Kleinstreuer, C. (2003). *Two-Phase Flow: Theory and Applications*. Taylor & Francis, New York.

Kleinstreuer, C., & Zhang, Z. (2003a). Laminar-to-turbulent fluid-particle flows in a human airway model. *Int. J. Multiphase Flow,* 29, 271-289.

Kleinstreuer, C., and Zhang, Z. (2003b). Targeted drug aerosol deposition analysis for a four-generation lung airway model with hemispherical tumors, *ASME Journal of Biomechanical Engineering,* 125(2), 197-206.

Ley, S., Mayer, D., Brook, B. S., Van Beek, E. J. R., Heussel, C. P., Rinck, D., Hose, R., Markstaller, K., & Kauczor, H.-U. (2002). Radiological imaging as the basis for a simulation software of ventilation in the tracheo-bronchial tree. *Eur. Ragiol.,* 12, 2218-2228.

Longest, P. W., Kleinstreuer, C. & Buchanan, J. R. (2004). Efficient computation of micro-particle dynamics including wall effects. *Computers & Fluids* (in press).

Makino E, Mitsuya T, and Shibata T (2001). Fabrication of {TiNi} shape memory micropump. *Sensors and Actuators A,* 88, 256--262.

Morris, I. R. (1988). Functional Anatomy of the Upper Airway, *Emerg. Med. Clin. North Am.* 6: 639-669.

Pitschellis R, Mechanische Miniaturgreifer mit Formgedachtnisantrieb (1998). No. 714 in Fortschr.-Ber. VDI Reihe 8. VDI Verlag Dusseldorf Raabe, O. G., Yeh, H. C., Schum, G. M. & Phalen, R. F. (1976), *Tracheobronchial Geometry: Human, Dog, Rat, Hamster, LF*-53. Lovelace Foundation Report, Albuquerque, N. Mex.

Reynaerts D, Peirs J, and van Brussel H (1999). Shape memory micro-actuation for a gastro-intestinal intervention system. *Sens Act,* 77, 157--166.

Schlesinger, R. B., Gurman, J. L. & Lippmann, M. (1982). Particle deposition within bronchial airways: Comparisons using constant and cyclic inspiratory flows, *Ann. Occup. Hyg.* 26, 47-64.

Seelecke S. Adaptive structures with SMA actuators—modeling und simulation (in German), Habilitation Thesis, TU Berlin, 1999.

Seelecke S. and Müller I. Shape memory alloy actuators in smart structures—modeling and simulation, Applied Mechanics Review, vol 57, no 1, 2004

Seelecke S. and Büskens C. Optimal control of beam structures by shape memory wires. In S. Hernandez and C. A. Brebbia, editors, Opti 97, Computer Aided Optimum Design of Structures, Rome, Italy, Sep. 8-10, 1997, pages 457-466, Rome, Italy, Sep. 8-10, 1997, Comp. Mech. Press, 1997.

Seelecke S. and Papenfuβ N. (1999). Simulation and Control of SMA Actuators, in *Proceedings of the 6th SPIE Conference on Smart Structures and Materials*, Vol. 3667, Newport Beach, USA, 1-5 Mar. 1999

Seelecke S., Papenfuβ N., A Finite Element Formulation for SMA Actuators, Journal of Applied Mechanics and Engineering, Vol. 5, No. 1, 2000

Seelecke S., Büskens C., Müller I., and Sprekels J., Online Optimization of Large Systems: State of the Art, chapter Real-Time Optimal Control of Shape Memory Alloy Actuators in Smart Structures, Springer Verlag, 2001.

Smith R. C. Inverse compensation for hysteresis in magnetostrictive transducers. Mathematical and Computer Modelling, 33:285-298, 2001.

Smith R. C., Seelecke S., Ounaies Z. and Smith J., A Free Energy Model for Hysteresis in Ferroelectric Materials, Journal of Intelligent Material Systems and Structures, 2003, submitted.

Smith R. C., Seelecke S., Dapino M. J. and Ounaies Z., Unified Model for Hysteresis in Ferroic Materials, SPIE Smart Structures and Materials 2003, Modeling, Signal Processing, and Control, San Diego, Calif., 2003, to appear.

Weibel, E. R. (1963). *Morphometry of the Human Lung*. New York: Academic Press.

Wilcox, D. C. (1998). *Turbulence Modeling for CFD (Second Edition)*, DCW Industries, Inc., LA Canada, CA.

Xu D, Wang L, Ding G, Zhou Y, Yu A, and Cai B (2001). Characteristics and fabrication of NiTi/Si diaphragm micropump. Sensors and Actuators A, 93, 87-92.

Zhang, L., Asgharian, B. & Anjilvel, S. (1996). Inertial and interceptional deposition of fibers in a bifurcating airway. *J. Aerosol Medicine* 9, 419-430.

Zhang, Z., & Kleinstreuer, C. (2002). Transient airflow structures and particle transport in a sequentially branching lung airway model. *Physics of Fluids,* 14, 862-880.

Zhang, Z. & Kleinstreuer, C. (2003a). Modeling of low Reynolds number turbulent flows in locally constricted conduits: A comparison study. *AIAA Journal,* 41, 831-840.

Zhang, Z. & Kleinstreuer, C (2003b). Species heat and mass transfer in a human upper airway model, *International Journal of Heat and Mass Transfer,* 46, 4755-4768.

Zhang, Z. & Kleinstreuer, C (2003c). Airflow structures and nano-particle deposition in a human upper airway model, *Journal of Computational Physics*, Submitted for publication.

Zhang, Z., Kleinstreuer, C. & Kim, C. S. (2001). Effects of curved inlet tubes on particle deposition in bifurcating lung airways. *Journal of Biomechanics*, 34, 659-669.

Zhang, Z., Kleinstreuer, C. & Kim, C. S., (2002a). Cyclic micron-size particle inhalation and deposition in a triple bifurcation lung airway model. *J. Aerosol Science* 33, 257-281.

Zhang, Z., Kleinstreuer, C. & Kim, C. S., (2002b). Aerosol deposition efficiencies and upstream release positions for different inhalation modes in an upper bronchial airway model. *Aerosol Science & Technology*, 36, 828-844.

Zhang, Z., Kleinstreuer, C., Kim, C. S. & Hickey, A. J. (2002c). Aerosol transport and deposition in a triple bifurcation bronchial airway model with local tumors. *Inhalation Toxicology*, 14, 1111-1133.

Zhang, Z., Kleinstreuer, C. & Kim, C. S. (2002d). Microparticle transport and deposition in a human oral airway model, *J. Aerosol Science*, 33, 1635-1652.

Zhang, Z., Kleinstreuer, C. & Kim, C. S. (2002e). Computational analysis of micron-particle deposition in a human triple bifurcation airway model, *Computer Methods in Biomechanics and Biomedical Engineering*, 5, 135-147.

Zhang, Z., Kleinstreuer, C. and Kim, C. S. (2002f). Gas-Solid Two-Phase Flow in a Triple Bifurcation Lung Airway Model, *Int. J. Multiphase Flow*, Vol. 28, pp. 1021-1046.

Zhang, Z., Kleinstreuer, C., Kim, C. S. & Cheng, Y. S. (2003a). Vaporizing micro-droplet inhalation, transport and deposition in a human upper airway model, *Aerosol Science and Technology*, (in press).

Zhang, Z., Kleinstreuer, C & Donohue, J. F. (2003b). Comparison of micro- and nano-size particle depositions in a human upper airway model, *Journal of Aerosol Science*, Submitted for publication.

Zhang, Z., Kleinstreuer, C, Donohue, J. F. and Kim, C. S. (2005). Comparison of Micro- and Nano-Size Particle Depositions in a Human Upper Airway Model, *Journal of Aerosol Science*, Vol. 36, 211-233.

It will be understood that various details of the presently disclosed subject matter may be changed without departing from the scope of the present subject matter. Furthermore, the foregoing description is for the purpose of illustration only, and not for the purpose of limitation.

What is claimed is:

1. A method of delivering an active agent to a target area of a lung of a subject in need thereof, comprising:
    (a) providing an inhaler system for directing to a subject a controlled aerosol stream comprising an active agent; wherein the inhaler system comprises:
        (1) an aerosol source;
        (2) an aerosol injection system in flow communication with the aerosol source; and
        (3) an inhaler device in flow communication with the aerosol injection system, comprising:
            (i) an outer tube having an inlet at one end, an outlet at an opposing end, and a wall joining the inlet and the outlet comprising one or more air inlet perforations which provide for passage of inhalation airflow into an interior of the outer tube;
            (ii) an inhalation airflow control mechanism for varying a cross-section of one or more of the outer tube air inlet perforations, thereby permitting control of the inhalation airflow to generate a desired inhalation waveform;
            (iii) an adaptive nozzle positioned within the interior of the outer tube and having a nozzle base inlet engaged with the outer tube inlet and a nozzle tip outlet proximal to the outer tube outlet, wherein the nozzle tip outlet and the nozzle base inlet are in flow communication and adapted for passage of an aerosol stream therebetween; and
            (iv) one or more actuators operationally linked to the adaptive nozzle, wherein the one or more actuators can position the nozzle tip outlet at a desired position in the outer tube outlet cross section and thereby control the position of aerosol stream release into the desired inhalation waveform from the inhaler device, wherein the aerosol stream is delivered into the inhalation waveform from the desired release position to deliver the active agent to a target area of a lung of the subject; and
    (b) regulating an inhalation waveform from the inhaler and a desired release position of the controlled aerosol stream into the inhalation waveform, wherein the aerosol stream is delivered into the inhalation waveform from the desired release position from the inhaler system to deliver the active agent to a target area of a lung of the subject.

2. The method of claim 1, wherein the active agent comprises one or more physical characteristics selected from the group consisting of: a particle size of from about 1 µm to about 20 µm; a substantially spherical shape; and a low density.

3. The method of claim 1, wherein the inhalation airflow control mechanism comprises:
    (i) an inner tube comprising one or more air inlet perforations, wherein the inner tube is positioned within the interior of the outer tube and slidingly engages an inner surface of the outer tube wall; and
    (ii) one or more actuators operationally linked to the inner tube, wherein the one or more actuators can slidingly position the inner tube to vary the alignment of the one or more inner tube air inlet perforations with the outer tube air inlet perforations, thereby varying the cross-section of one or more of the outer tube air inlet perforations.

4. The method of claim 3, comprising regulating a position of the inner tube within the outer tube and the position of the adaptive nozzle utilizing a control logic.

5. The method of claim 4, wherein the control logic comprises a proportional-integral-derivative (PID) algorithm.

6. The method of claim 4, wherein the control logic is in operational communication with computational fluid-particle dynamics results that determine one or more of the desired inhalation waveforms and the desired position of the adaptive nozzle to control the release position of the aerosol stream into the desired inhalation waveform to direct the active agent to the target area of the lung of the subject.

7. The method of claim 4, wherein the inhaler device comprises one or more micropressure sensors positioned proximal to the outer tube outlet, which can detect an inhalation waveform from inhalation airflow flowing through the outer tube and transmit a signal to the inner tube actuators, wherein the signal from the micropressure sensors is transmitted to the control logic which interprets the signal and transmits an actuator control signal to the inner tube actuators which vary the position of the inner tube to change the alignment of the inner tube air inlet perforations with the outer tube air inlet perforations, thereby altering the inhalation waveform in response to the signal.

8. The method of claim 3, wherein the one or more inner tube actuators and the one or more adaptive nozzle actuators comprise an active material.

9. The method of claim 8, wherein the active material is independently selected from the group consisting of a shape memory alloy, a shape memory polymer, a magnetostrictive material, and a piezoceramic material.

10. The method of claim 9, wherein the shape memory alloy comprises an alloy of nickel and titanium (NiTi).

11. An inhaler device for targeted aerosol stream release, comprising:
   (a) an outer tube having an inlet at one end, an outlet at an opposing end, and a wall joining the inlet and the outlet comprising one or more air inlet perforations which provide for passage of inhalation airflow into an interior of the outer tube;
   (b) an inhalation airflow control mechanism for varying a cross-section of one or more of the outer tube air inlet perforations, thereby permitting control of the inhalation airflow to generate a desired inhalation waveform;
   (c) an adaptive nozzle positioned within the interior of the outer tube and having a nozzle base inlet engaged with the outer tube inlet and a nozzle tip outlet proximal to the outer tube outlet, wherein the nozzle tip outlet and the nozzle base inlet are in flow communication and adapted for passage of an aerosol stream therebetween; and
   (d) one or more actuators operationally linked to the adaptive nozzle, wherein the one or more actuators can position the nozzle tip outlet at a desired position in the outer tube outlet cross section and thereby control the position of aerosol stream release into the desired inhalation waveform from the inhaler device, wherein the aerosol stream is delivered into the inhalation waveform from a desired release position for targeted aerosol stream release.

12. The inhaler device of claim 11, wherein the inhalation airflow control mechanism comprises:
   (a) an inner tube comprising one or more air inlet perforations, wherein the inner tube is positioned within the interior of the outer tube and slidingly engages an inner surface of the outer tube wall; and
   (b) one or more actuators operationally linked to the inner tube, wherein the one or more actuators can slidingly position the inner tube to vary the alignment of the one or more inner tube air inlet perforations with the outer tube air inlet perforations, thereby varying the cross-section of one or more of the outer tube air inlet perforations.

13. The inhaler device of claim 12, wherein the one or more inner tube actuators comprise an active material.

14. The inhaler device of claim 13, wherein the active material is selected from the group consisting of a shape memory alloy, a shape memory polymer, a magnetostrictive material, and a piezoceramic material.

15. The inhaler device of claim 14, wherein the shape memory alloy comprises an alloy of nickel and titanium (NiTi).

16. The inhaler device of claim 12, comprising one or more micropressure sensors positioned proximal to the outer tube outlet, which can detect an inhalation waveform from inhalation airflow flowing through the outer tube and transmit a signal to the inner tube actuators, wherein the inner tube actuators vary the position of the inner tube to change the alignment of the inner tube air inlet perforations with the outer tube air inlet perforations, thereby altering the inhalation waveform in response to the signal.

17. The inhaler device of claim 16, wherein the signal from the micropressure sensors is transmitted to a control logic which interprets the signal and transmits an actuator control signal to the inner tube actuators.

18. The inhaler device of claim 17, wherein the control logic comprises a proportional-integral-derivative (PID) algorithm.

19. The inhaler device of claim 17, wherein the control logic is in operational communication with computational fluid-particle dynamics results that determine one or more of the desired inhalation waveform and the desired position of the adaptive nozzle to control the release position of the aerosol stream into the desired inhalation waveform to direct the aerosol stream to a desired target area in a lung of a subject.

20. The inhaler device of claim 11, wherein the adaptive nozzle comprises a flexible polymer that permits flexing of the adaptive nozzle.

21. The inhaler device of claim 20, wherein the one or more adaptive nozzle actuators comprise a first set of adaptive nozzle actuators that position the nozzle tip outlet within the outer tube and a second set of adaptive nozzle actuators that flex the adaptive nozzle such that the nozzle tip outlet is axially aligned with the outer tube outlet after positioning.

22. The inhaler device of claim 11, wherein the one or more adaptive nozzle actuators comprise an active material.

23. The inhaler device of claim 22, wherein the active material is selected from the group consisting of a shape memory alloy, a shape memory polymer, a magnetostrictive material, and a piezoceramic material.

24. The inhaler device of claim 23, wherein the shape memory alloy comprises an alloy of nickel and titanium (NiTi).

25. The inhaler device of claim 11, wherein the adaptive nozzle can be rotated in an orbit around a central long axis of the outer tube and positioned at one or more desired orbital locations on the orbit.

26. An inhaler system for targeted aerosol stream release, comprising:
   (a) an aerosol source;
   (b) an aerosol injection system in flow communication with the aerosol source; and
   (c) an inhaler device in flow communication with the aerosol injection system, comprising:
      (i) an outer tube having an inlet at one end, an outlet at an opposing end, and a wall joining the inlet and the outlet comprising one or more air inlet perforations which provide for passage of inhalation airflow into an interior of the outer tube;
      (ii) an inhalation airflow control mechanism for varying a cross-section of one or more of the outer tube air inlet perforations, thereby permitting control of the inhalation airflow to generate a desired inhalation waveform;
      (iii) an adaptive nozzle positioned within the interior of the outer tube and having a nozzle base inlet engaged with the outer tube inlet and a nozzle tip outlet proximal to the outer tube outlet, wherein the nozzle tip outlet and the nozzle base inlet are in flow communication and adapted for passage of an aerosol stream therebetween; and
      (iv) one or more actuators operationally linked to the adaptive nozzle, wherein the one or more actuators can position the nozzle tip outlet at a desired position in the outer tube outlet cross section and thereby control the position of aerosol stream release into the desired inhalation waveform from the inhaler device, wherein the aerosol stream is delivered into the inhalation waveform from a desired release position for targeted aerosol stream release.

27. The inhaler system of claim 26, wherein the aerosol source comprises a source selected from the group consisting of a pressurized metered dose inhaler (pMDI), a jet nebulizer (JN) and a dry powder inhaler (DPI).

28. The inhaler system of claim 26, wherein the aerosol injection system comprises a controllable reservoir chamber having an inlet in flow communication with the aerosol source and an outlet in flow communication with the inhaler device.

29. The inhaler system of claim 26, wherein the aerosol injection system comprises:
  (d) a pressure sensor that measures pressure within the controllable reservoir chamber;
  (e) an inlet valve for controlling entry of an aerosol into the controllable reservoir chamber through the reservoir chamber inlet; and
  (f) an outlet valve for controlling release of the aerosol from the controllable reservoir chamber through the reservoir chamber outlet, wherein the pressure sensor measures pressure within the reservoir chamber and regulates opening and closing of the inlet valve and the outlet valve in order to maintain a desired pressure within the reservoir chamber.

30. The inhaler system of claim 29, wherein the inlet and outlet valves each comprise an active material actuator.

31. The inhaler system of claim 30, wherein the active material actuator is a thin film actuator.

32. The inhaler system of claim 30, wherein the active material actuator comprises an active material selected from the group consisting of a shape memory alloy, a shape memory polymer, a magnetostrictive material, and a piezoceramic material.

33. The inhaler system of claim 26, wherein the inhalation airflow control mechanism comprises:
  (i) an inner tube comprising one or more air inlet perforations, wherein the inner tube is positioned within the interior of the outer tube and slidingly engages an inner surface of the outer tube wall; and
  (ii) one or more actuators operationally linked to the inner tube, wherein the one or more actuators can slidingly position the inner tube to vary the alignment of the one or more inner tube air inlet perforations with the outer tube air inlet perforations, thereby varying the cross-section of one or more of the outer tube air inlet perforations.

34. The inhaler system of claim 33, wherein the one or more inner tube actuators comprise an active material.

35. The inhaler system of claim 34, wherein the active material is selected from the group consisting of a shape memory alloy, a shape memory polymer, a magnetostrictive material, and a piezoceramic material.

36. The inhaler system of claim 35, wherein the shape memory alloy comprises an alloy of nickel and titanium (NiTi).

37. The inhaler system of claim 33, comprising one or more micropressure sensors positioned proximal to the outer tube outlet, which can detect an inhalation waveform from inhalation airflow flowing through the outer tube and transmit a signal to the inner tube actuators, wherein the inner tube actuators vary the position of the inner tube to change the alignment of the inner tube air inlet perforations with the outer tube air inlet perforations, thereby altering the inhalation waveform in response to the signal.

38. The inhaler system of claim 37, wherein the signal from the micropressure sensors is transmitted to a control logic which interprets the signal and transmits an actuator control signal to the inner tube actuators.

39. The inhaler system of claim 38, wherein the control logic comprises a proportional-integral-derivative (PID) algorithm.

40. The inhaler system of claim 39, wherein the control logic is in operational communication with computational fluid-particle dynamics results that determine one or more of the desired inhalation waveform and the desired position of the adaptive nozzle to control the release position of the aerosol stream into the desired inhalation waveform to direct the aerosol stream to a desired target area in a lung of a subject.

41. The inhaler system of claim 26, wherein the adaptive nozzle comprises a flexible polymer that permits flexing of the adaptive nozzle.

42. The inhaler system of claim 41, wherein the one or more adaptive nozzle actuators comprise a first set of adaptive nozzle actuators that position the nozzle tip outlet within the outer tube and a second set of adaptive nozzle actuators that flex the adaptive nozzle such that the nozzle tip outlet is axially aligned with the outer tube outlet after positioning.

43. The inhaler system of claim 42, wherein the one or more adaptive nozzle actuators comprise an active material.

44. The inhaler system of claim 43, wherein the active material is selected from the group consisting of a shape memory alloy, a shape memory polymer, a magnetostrictive material, and a piezoceramic material.

45. The inhaler system of claim 44, wherein the shape memory alloy comprises an alloy of nickel and titanium (NiTi).

46. The inhaler system of claim 26, wherein the adaptive nozzle can be rotated in an orbit about a central long axis of the outer tube and positioned at one or more desired orbital locations on the orbit.

* * * * *